(12) United States Patent
Liu et al.

(10) Patent No.: US 11,497,771 B2
(45) Date of Patent: Nov. 15, 2022

(54) PLASMID COMBINATION AND APPLICATION THEREOF IN PREPARING MODIFIED IMMUNE CELLS

(71) Applicant: JUVENTAS CELL THERAPY LTD., Tianjin (CN)

(72) Inventors: Yun Liu, Tianjin (CN); Lin Shi, Tianjin (CN); Lulu Lv, Tianjin (CN); Pan Xie, Tianjin (CN); Mengmeng Cao, Tianjin (CN); Wang Yang, Tianjin (CN); Jiaxing Yang, Tianjin (CN); Fei Wang, Tianjin (CN); Rui Wang, Tianjin (CN)

(73) Assignee: JUVENTAS CELL THERAPY LTD., Tianjin (CN)

( * ) Notice: Subject to any disclaimer, the term of this patent is extended or adjusted under 35 U.S.C. 154(b) by 0 days.

(21) Appl. No.: 17/412,617

(22) Filed: Aug. 26, 2021

(65) Prior Publication Data

US 2022/0040233 A1 Feb. 10, 2022

Related U.S. Application Data

(63) Continuation of application No. PCT/CN2020/136542, filed on Dec. 15, 2020.

(51) Int. Cl.
| | |
|---|---|
| C12N 15/86 | (2006.01) |
| A61K 35/17 | (2015.01) |
| A61P 35/02 | (2006.01) |
| C07K 14/705 | (2006.01) |
| C07K 16/28 | (2006.01) |

(52) U.S. Cl.
CPC .............. *A61K 35/17* (2013.01); *A61P 35/02* (2018.01); *C07K 14/70517* (2013.01); *C07K 14/70521* (2013.01); *C07K 14/70578* (2013.01); *C07K 16/2803* (2013.01); *C07K 16/2887* (2013.01); *C12N 15/86* (2013.01)

(58) Field of Classification Search
None
See application file for complete search history.

(56) References Cited

U.S. PATENT DOCUMENTS

| | | | | |
|---|---|---|---|---|
| 2011/0300543 A1* | 12/2011 | Wang | ................... | C12N 5/0696 435/7.1 |
| 2014/0271818 A1* | 9/2014 | James | ................ | C12N 15/1138 435/320.1 |
| 2015/0190428 A1* | 7/2015 | June | ....................... | G01N 33/92 435/6.12 |
| 2019/0201517 A1* | 7/2019 | Bouckenooghe | ....... | A61P 43/00 |
| 2020/0109210 A1 | 4/2020 | Lentigen | | |
| 2021/0236549 A1 | 8/2021 | Immunotech | | |

FOREIGN PATENT DOCUMENTS

| | | |
|---|---|---|
| CN | 1919871 A | 2/2007 |
| CN | 104788573 A | 7/2015 |
| CN | 106191218 A | 12/2016 |
| CN | 108531457 A | 9/2018 |
| CN | 108707625 A | 10/2018 |
| CN | 109609465 A | 4/2019 |
| CN | 110404061 A | 11/2019 |
| CN | 110467675 A | 11/2019 |
| CN | 110592023 A | 12/2019 |
| CN | 111183156 A | 5/2020 |
| CN | 112079934 A | 12/2020 |
| CN | 112226463 A | 1/2021 |
| WO | WO 2018/102769 A1 | 6/2018 |

OTHER PUBLICATIONS

Translation of the International Search Report for PCT Application No. PCT/CN2020/136542, dated Mar. 12, 2021 (four pages).

Zhitao Ying, et al. "Parallel Comparison of 4-1BB or CD28 Co-Stimulated CD19-Targeted CAR-T Cells for B Cell Non-Hodgkin's Lymphoma," Molecular Therapy Oncolytics, vol. 15, pp. 60-68 (2019).

* cited by examiner

*Primary Examiner* — Michail A Belyavskyi

(74) *Attorney, Agent, or Firm* — Finnegan, Henderson, Farabow, Garrett & Dunner LLP

(57) ABSTRACT

Provided in the present disclosure is a method for using a four-plasmid system to prepare modified immune effector cells. The method comprises: forming a lentivirus by using four plasmids within 293T cells, extracting and obtaining the lentivirus, then transfecting immune effector cells by using the lentivirus, and expressing a chimeric antigen receptor. Also provided in the present disclosure is a use of the immune effector cell obtained by using the described method and of a composition containing the immune effector cell.

17 Claims, 8 Drawing Sheets
Specification includes a Sequence Listing.

SEQUENCE LISTING

<160> NUMBER OF SEQ ID NOS: 2

<210> SEQ ID NO 1
<211> LENGTH: 493

<212> TYPE: PRT
<213> ORGANISM: Artificial Sequence
<220> FEATURE:
<223> OTHER INFORMATION: Tn Amino Acid Sequence of The Chimeric Antigen Receptor

<400> SEQUENCE: 1

```
Met Ala Leu Pro Val Thr Ala Leu Leu Leu Pro Leu Ala Leu Leu Leu
1               5                   10                  15

His Ala Ala Arg Pro Gly Ser Asp Ile Val Leu Thr Gln Ser Pro Lys
            20                  25                  30

Phe Met Ser Thr Ser Val Gly Asp Arg Val Ser Val Thr Cys Lys Ala
        35                  40                  45

Ser Gln Asn Val Gly Thr Asn Val Ala Trp Tyr Gln Gln Lys Pro Gly
    50                  55                  60

Gln Ser Pro Lys Pro Leu Ile Tyr Ser Ala Thr Tyr Arg Asn Ser Gly
65                  70                  75                  80

Val Pro Asp Arg Phe Thr Gly Ser Gly Ser Gly Thr Asp Phe Thr Leu
                85                  90                  95

Thr Ile Thr Asn Val Gln Ser Lys Asp Leu Ala Asp Tyr Phe Cys Gln
            100                 105                 110

Gln Tyr Asn Arg Tyr Pro Tyr Thr Ser Gly Gly Gly Thr Lys Leu Glu
        115                 120                 125

Ile Lys Arg Gly Gly Gly Gly Ser Gly Gly Gly Gly Ser Gly Gly Gly
    130                 135                 140

Gly Ser Gln Val Gln Leu Gln Gln Ser Gly Ala Glu Leu Val Arg Pro
145                 150                 155                 160

Gly Ser Ser Val Lys Ile Ser Cys Lys Ala Ser Gly Tyr Ala Phe Ser
                165                 170                 175

Ser Tyr Trp Met Asn Trp Val Lys Gln Arg Pro Gly Gln Gly Leu Glu
            180                 185                 190

Trp Ile Gly Gln Ile Tyr Pro Gly Asp Gly Asp Thr Asn Tyr Asn Gly
        195                 200                 205

Lys Phe Lys Gly Gln Ala Thr Leu Thr Ala Asp Lys Ser Ser Ser Thr
    210                 215                 220

Ala Tyr Met Gln Leu Ser Gly Leu Thr Ser Glu Asp Ser Ala Val Tyr
225                 230                 235                 240

Phe Cys Ala Arg Lys Thr Ile Ser Ser Val Val Asp Phe Tyr Phe Asp
                245                 250                 255

Tyr Trp Gly Gln Gly Thr Thr Leu Thr Val Ser Ser Glu Phe Thr Thr
            260                 265                 270

Thr Pro Ala Pro Arg Pro Pro Thr Pro Ala Pro Thr Ile Ala Ser Gln
        275                 280                 285

Pro Leu Ser Leu Arg Pro Glu Ala Cys Arg Pro Ala Ala Gly Gly Ala
    290                 295                 300

Val His Thr Arg Gly Leu Asp Phe Ala Cys Asp Ile Tyr Ile Trp Ala
305                 310                 315                 320

Pro Leu Ala Gly Thr Cys Gly Val Leu Leu Leu Ser Leu Val Ile Thr
                325                 330                 335

Leu Tyr Cys Lys Arg Gly Arg Lys Lys Leu Leu Tyr Ile Phe Lys Gln
            340                 345                 350

Pro Phe Met Arg Pro Val Gln Thr Thr Gln Glu Glu Asp Gly Cys Ser
        355                 360                 365

Cys Arg Phe Pro Glu Glu Glu Glu Gly Gly Cys Glu Leu Arg Val Lys
    370                 375                 380
```

Phe Ser Arg Ser Ala Asp Ala Pro Ala Tyr Gln Gln Gly Gln Asn Gln
385                 390                 395                 400

Leu Tyr Asn Glu Leu Asn Leu Gly Arg Arg Glu Glu Tyr Asp Val Leu
            405                 410                 415

Asp Lys Arg Arg Gly Arg Asp Pro Glu Met Gly Gly Lys Pro Arg Arg
        420                 425                 430

Lys Asn Pro Gln Glu Gly Leu Tyr Asn Glu Leu Gln Lys Asp Lys Met
    435                 440                 445

Ala Glu Ala Tyr Ser Glu Ile Gly Met Lys Gly Glu Arg Arg Arg Gly
450                 455                 460

Lys Gly His Asp Gly Leu Tyr Gln Gly Leu Ser Thr Ala Thr Lys Asp
465                 470                 475                 480

Thr Tyr Asp Ala Leu His Met Gln Ala Leu Pro Pro Arg
            485                 490

<210> SEQ ID NO 2
<211> LENGTH: 1482
<212> TYPE: DNA
<213> ORGANISM: Artificial Sequence
<220> FEATURE:
<223> OTHER INFORMATION: The Nucleic Acid Sequence Ecoding The Chimeric
      Antigen Receptor

<400> SEQUENCE: 2
atggccttac cagtgaccgc cttgctcctg ccgctggcct tgctgctcca cgccgccagg      60
ccgggatccg atattgtgct gacccagagc cccaagttca tgagcaccag cgtgggcgat    120
agagtgagcg tgacctgcaa ggcaagccag aacgtgggaa caaacgtggc ctggtaccaa    180
cagaaacccg gccaaagccc taagcccctg atttacagcg ccacctacag aaatagcggc    240
gtgcccgaca gatttacagg aagcggcagc ggaaccgatt tcacactgac catcaccaac    300
gtgcagagca agacctggc cgactacttc tgccagcagt acaacagata ccccctacacc    360 agcggaggag aacaaagct ggagatcaag agaggtggtg gtggttctgg cggcggcggc    420
tccggtggtg gtggttctca gtgcaactg aacagagcg agccgaact ggtgagaccc    480 ggaagcagcg tgaagatcag ctgcaaggct ccggctacg cctttagcag ctactggatg    540
aactgggtga agcagagacc tggacaggga ctggaatgga tcggccagat ttaccctgga    600
gacggcgaca caaactacaa cggcaagttc aagggccaag ctacactgac cgccgacaaa    660
agcagcagca ccgcctatat gcagctgagc ggactgacca cgcaagatag cgctgtgtac    720
ttctgcgcca gaaagaccat cagcagcgtg gtggacttct acttcgacta ctggggacaa    780
ggcaccaccc tgacagtgag cagcgaattc accacgacgc cagcgccgcg accaccaaca    840
ccggcgccca ccatcgcgtc gcagcccctg tccctgcgcc cagaggcgtg ccggccagcg    900
gcggggggcg cagtgcacac gagggggctg gacttcgcct gtgatatcta catctggggcg    960 cccttggccg ggacttgtgg ggtccttctc ctgtcactgg ttatcaccct ttactgcaaa   1020
cggggcagaa agaaactcct gtatatattc aaacaaccat ttatgagacc agtacaaact   1080
actcaagagg aagatggctg tagctgccga tttccagaag aagaagaagg aggatgtgaa   1140
ctgagagtga agttcagcag gagcgcagac gcccccgcgt accagcaggg ccagaaccag   1200
ctctataacg agctcaatct aggacgaaga gaggagtacg atgttttgga caagagacgt   1260

```
                                           -continued ggccgggacc ctgagatggg gggaaagccg agaaggaaga accctcagga aggcctgtac      1320
aatgaactgc agaaagataa gatggcggag gcctacagtg agattgggat gaaaggcgag      1380
cgccggaggg gcaaggggca cgatggcctt taccagggtc tcagtacagc caccaaggac      1440
acctacgacg cccttcacat gcaggccctg cccctcgct aa                         1482
```

PLASMID COMBINATION AND APPLICATION THEREOF IN PREPARING MODIFIED IMMUNE CELLS

This application is a continuation of International Application No. PCT/CN2020/136542, filed on Dec. 15, 2020, which claims priority of Chinese Patent Application No. CN 201911301518.8, filed on Dec. 17, 2019, of Chinese Patent Application No. CN 202011274810.8, filed Nov. 16, 2020, and of Chinese Patent Application No. CN 202011433671.9, filed on Dec. 10, 2020. The contents of each of these applications are incorporated herein by reference in their entirety.

FIELD OF THE INVENTION

The present disclosure relates to the field of biomedicine. More specifically, the present disclosure relates to a method for transfecting 293T cells using a four-plasmid system, comprising forming a lentivirus by using four plasmids within 293T cells, extracting and obtaining the lentivirus, and then transfecting the T cells with the lentivirus to express a chimera antigen receptor targeting CD19. The present disclosure further relates to an immune effector cell obtained by using the method, a composition comprising the immune effector cell, and use thereof.

BACKGROUND OF THE INVENTION

At present, clinical treatment for acute lymphoblastic leukemia (ALL), chronic lymphocytic leukemia (CLL) and B-cell lymphoma mainly includes chemotherapy, stem cell transplantation, and biological therapy. Although such therapies can achieve certain efficacy, relapsed or refractory leukemia still remains as a major issue difficult to be tackled. As a new treatment strategy, cellular immunotherapy of tumor has become a hot topic in recent researches. CD19 is widely expressed on the surface of almost all the B-cell tumor cells, while being rarely expressed in other parenchymal cells and hematopoietic stem cells.

Tumor cells can produce immune escape by various pathways, e.g., down-regulating expression of the molecules that participate in T cell recognition and antigen responses, or reducing immunogenicity, thereby enabling the immune system of an organism to be incapable of removing tumors effectively. Studies have found that chimeric antigen receptor T cells (CAR-T cells) can recognize antigens on the surface of tumor cells and specifically kill the tumor cells, and thus they are useful for the treatment of tumors.

Lentiviruses prepared using a plasmid packaging system that are currently available in the prior art have a low concentration of viable viruses and a low transfection titer. To achieve an ideal effect of T cell transfection, it is necessary to add a much higher dose of lentiviruses with the disadvantages of higher costs, excess residual substances and poor safety performance. In spite of the fact that four-plasmid packaging system has also been used in the prior art to replace the three-plasmid packaging system, the proper ratio at which the plasmids can be combined to provide higher transfection titer while ensuring good safety performance has not been determined yet. Thus, there remains an urgent need to screen a suitable ratio of the four plasmids for packaging lentiviral vectors to prepare modified immune effector cells.

SUMMARY OF THE INVENTION

To overcome the disadvantages of the prior art, the present disclosure provides a four-plasmid packaging system composed of a target plasmid and three helper plasmids, wherein the target plasmid is freed from non-essential components for virus packaging, thereby effectively minimizing potential safety hazards. By using four plasmids at particular ratios, the present disclosure can effectively increase the transfection titer of the obtained lentivirus, and provide CAR-T cells that exhibit excellent clinical therapeutic effects and higher safety performance obtained by transfecting the T cells with lentiviral vectors loaded with particular CAR.

The present disclosure provides a chimeric antigen receptor, comprising an amino acid sequence shown in SEQ ID NO. 1. The present disclosure further provides a nucleic acid encoding the chimeric antigen receptor, a vector comprising the nucleic acid, an immune effector cell comprising the chimeric antigen receptor, the nucleic acid molecule and/or the vector, a method for preparing the immune effector cell, a composition comprising the immune effector cell, and use of the chimeric antigen receptor.

The chimeric antigen receptor according to the present disclosure at least comprises one of the following advantageous effects:

(1) stable expression on the surface of immune cells (such as T cells), at high expression levels;

(2) a strong ability to kill CD19-positive target cells;

(3) an ability to promote immune cells to secrete cytokines, e.g., enhancing the ability of T cells to secrete cytokines (INF-γ or IL-6) by at least 1, 2, or 3 times;

(4) being non-hemolytic, and not susceptible to induce hemolysis or aggregation of red blood cells;

(5) being vascular irritation-free, and resulting in no local or systemic abnormalities after administration;

(6) being devoid of oncogenic potential, and non-oncogenic in vivo or in vitro;

(7) an ability to prolong the survival time of cancer patients;

(8) an ability to effectively ameliorate the severity of cancer (such as acute lymphoblastic leukemia in adults, acute lymphoblastic leukemia in children and/or non-Hodgkin's lymphoma); and (9) an ability to exhibit higher safety performance with a lower risk of inducing side effects (e.g., cytokine release syndrome or CAR-T-cell-related encephalopathy syndrome).

In one aspect, the present disclosure provides a plasmid combination, wherein the plasmid combination comprises plasmids Seq1, PMD2.G, pMDLg-pRRE and pRSV-Rev; and the plasmids Seq1, PMD2.G, pMDLg-pRRE and pRSV-Rev are present at a ratio of 2-6: 1-1.5: 1-3: 1-1.5.

In certain embodiments, the plasmid Seq1 in the plasmid combination comprises a nucleic acid molecule encoding the chimeric antigen receptor, wherein the chimeric antigen receptor comprises an amino acid sequence shown in SEQ ID NO. 1.

In certain embodiments, the plasmid Seq1 in the plasmid combination comprises a nucleic acid molecule encoding the chimeric antigen receptor, wherein the nucleic acid molecule comprises a nucleic acid sequence shown in SEQ ID NO. 2.

In certain embodiments, the plasmids Seq1, PMD2.G, pMDLg-pRRE and pRSV-Rev in the plasmid combination are present at a ratio of 11.8: 3.53: 6.33: 2.3, 13.8: 3.48: 5.31: 2.54 or 14: 4.67: 4.67: 4.67.

In one aspect, the present disclosure provides a method for preparing a lentiviral vector, the method comprising the step of introducing the plasmid combination into a cell. In certain embodiments, the step of introducing refers to the step of transfecting.

In one aspect, the present disclosure provides a method for obtaining a lentiviral vector by transfecting cells with a four-plasmid packaging system, wherein the plasmid packaging system comprises plasmids Seq1, PMD2.G, pMDLg-pRRE and pRSV-Rev, and the plasmids Seq1, PMD2.G, pMDLg-pRRE and pRSV-Rev are present at a ratio of 2-6: 1-1.5: 1-3: 1-1.5.

In certain embodiments, the plasmid Seq1 can express a chimeric antigen receptor, comprising an amino acid sequence shown in SEQ ID NO.1.

In certain embodiments, the plasmid Seq1 comprises an isolated nucleic acid molecule encoding a chimeric antigen receptor, wherein the nucleic acid molecule comprises a nucleic acid sequence shown in SEQ ID NO.2.

In certain embodiments, the plasmids Seq1, PMD2.G, pMDLg-pRRE and pRSV-Rev are present at a ratio of 11.8: 3.53: 6.33: 2.3 or 13.8: 3.48: 5.31: 2.54.

In certain embodiments, the cell is 293T. In certain embodiments, the cell is 293T/17.

In one aspect, the present disclosure provides a chimeric antigen receptor, comprising an amino acid sequence shown in SEQ ID NO. 1.

In another aspect, the present disclosure further provides an isolated nucleic acid molecule encoding the chimeric antigen receptor described herein.

In another aspect, the present disclosure further provides an isolated nucleic acid molecule encoding a chimeric antigen receptor, wherein the nucleic acid molecule comprises a nucleic acid sequence shown in SEQ ID NO. 2.

In another aspect, the present disclosure further provides a plasmid comprising the nucleic acid molecule described herein.

In another aspect, the present disclosure further provides a method for preparing a modified immune effector cell, comprising the step of preparing and obtaining the lentiviral vector according to the method for preparing a lentivirus.

In certain embodiments, the method further comprises the step of introducing the lentiviral vector into an immune effector cell. In certain embodiments, the step of introducing refers to the step of transfecting.

In certain embodiments, the immune effector cell is selected from the group consisting of a T lymphocyte and a natural killer cell.

In another aspect, the present disclosure further provides a modified immune effector cell comprising the modified immune effector cell prepared and obtained by the method for preparing the modified immune effector cell.

In certain embodiments, the immune effector cells are selected from the group consisting of T lymphocytes and natural killer cells.

In certain embodiments, the immune effector cells can express the chimeric antigen receptor described herein.

In another aspect, the present disclosure further provides a composition comprising the modified immune effector cells obtained by the method described herein.

In certain embodiments, the immune effector cell is selected from the group consisting of T lymphocytes and natural killer cells.

In certain embodiments, the chimeric antigen receptor described herein is expressed on the surface of the immune effector cell.

In another aspect, the present disclosure further provides use of the immune effector cell prepared by the method, and/or the composition comprising the immune effector cell, the chimeric antigen receptor, the nucleic acid molecule, the vector and/or the immune effector cell in the manufacture of a medicament, wherein the medicament is useful for the treatment of a disease or disorder associated with CD19 expression.

In another aspect, the present disclosure further provides a method for the treatment of a disease or disorder associated with CD19 expression, comprising applying the composition and/or the immune effector cell.

In another aspect, the present disclosure further provides the composition and/or the immune effector cell for use in the treatment of a disease or disorder associated with CD19 expression.

In certain embodiments, the disease or disorder associated with CD19 expression comprises non-solid tumors.

In certain embodiments, the non-solid tumor comprises leukemia and/or lymphoma.

In certain embodiments, the disease or disorder associated with CD19 expression comprises acute lymphoblastic leukemia and/or B-cell lymphoma.

In certain embodiments, the acute lymphoblastic leukemia comprises acute lymphoblastic leukemia in adults and/or acute lymphoblastic leukemia in children.

In certain embodiments, the medicament for treating acute lymphoblastic leukemia is administered at a dose of $0.25 \times 10^8$ to $0.5 \times 10^8$ CAR-positive T cells.

In certain embodiments, the B-cell lymphoma comprises non-Hodgkin's lymphoma.

In certain embodiments, the medicament for treating non-Hodgkin's lymphoma is administered at a dose of $1 \times 10^8$ to $2 \times 10^8$ CAR-positive T cells.

Persons skilled in the art can easily perceive other aspects and advantages of the present disclosure from the detailed description below. In the following detailed description, only exemplary embodiments of the present disclosure are shown and described. As persons skilled in the art will recognize, the contents of this disclosure enable persons skilled in the art to make modifications to the specific embodiments disclosed herein without departing from the inventive spirit and scope of this disclosure. Correspondingly, the drawings and illustrations in the description of the present disclosure are only exemplary, rather than restrictive.

BRIEF DESCRIPTION OF THE DRAWINGS

The specific features involved in this disclosure are shown in the appended claims. The characteristics and advantages of the disclosure involved herein can be better understood by referring to the exemplary embodiments and the accompanying drawings described in detail below. A brief description of the drawings is as follows:

DETAILED DESCRIPTION OF THE INVENTION

Figure 1A:
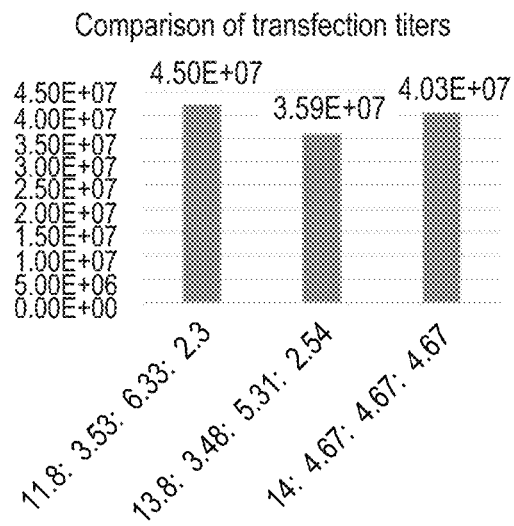
FIG. 1A shows the transfection titer after the transfection with the four-plasmid system.

The following specific examples illustrate the particular embodiments of the disclosure. Persons familiar with this technology can easily understand the other advantages and effects of the disclosure from the contents disclosed herein.

Hereinafter, the disclosure is further described: according to the present disclosure, unless otherwise specified, the scientific and technical terms used herein have the meanings commonly understood by those skilled in the art. In addition, the related terms and laboratory procedures of protein and nucleic acid chemistry, molecular biology, cell and tissue culture, microbiology, and immunology used herein are all terms and routine procedures widely used in the corresponding fields. In the meantime, to better understand the present disclosure, definitions and explanations of the related terms are provided below.

As used herein, the term "Chimeric Antigen Receptor" (CAR) generally refers to a fused protein comprising an extracellular domain capable of binding to an antigen and at least one intracellular domain. CAR is a core component of chimeric antigen receptor T cells (CAR-T), which may include a targeting moiety (for example, a moiety binding a tumor-associated antigen (TAA)), a hinge region, a transmembrane region, and an intracellular domain. In the present disclosure, the CAR may be combined with the intracellular domain for T cell receptor activation based on the antigen specificity of an antibody. T cells expressing CAR can specifically recognize and eliminate malignant cells expressing the target antigen.

As used herein, the term "isolated" generally refers to being obtained by artificial means from the natural state. If certain "isolated" substance or component appears in nature, it might mean that either the natural environment in which it is located has been changed, or the substance has been isolated from the natural environment, or both. For example, certain non-isolated polynucleotide or polypeptide naturally occurs in a living animal, and the same polynucleotide or polypeptide having high purity and isolated from this natural state is called as the isolated one. The term "isolated" does not exclude the occasion of being mixed with an artificial or synthetic substance, nor exclude the presence of other impurities that do not impair the activity of the substance.

As used herein, the term "immune effector cell" generally refers to cells that participate in an immune response, such as those promoting an immune effector response. In the present disclosure, the immune effector cell may be selected from the group consisting of T lymphocytes and natural killer cells.

As used herein, the term "specifically binds and/or specifically recognizes" generally refers to an interaction that is measurable and reproducible, such as the binding between a target and an antibody (or CAR structural fragment), which may determine the presence of a target when a heterogeneous cell population of a molecule (including a biomolecule) exists. For example, an antibody (or CAR structural fragment) that specifically binds to a target (which may be an epitope) is the antibody (or CAR structural fragment) that binds to the target with higher affinity and avidity, in an easier manner and/or for a longer duration, compared with its binding to other targets.

As used herein, the term "isolated nucleic acid molecule" generally refers to a nucleotide, deoxyribonucleotide or ribonucleotide of any length in its isolated form, or an analog that has been isolated from their natural environment or artificially synthesized.

As used herein, the term "plasmid" or "vector" generally refers to a tool for delivering nucleic acid into which a polynucleotide encoding certain protein can be inserted and by which the protein can be expressed. The vector can be transformed, transduced or transfected into the host cell so that the genetic material element it carries can be expressed in the host cell. For example, vectors include a plasmid; a phagemid; a cosmid; an artificial chromosome (such as yeast artificial chromosome (YAC), a bacterial artificial chromosome (BAC) or a P1-derived artificial chromosome (PAC)); a phage such as λ phage or M13 phage and an animal virus, etc. The types of animal viruses as the vector include retrovirus (including lentivirus), adenovirus, adeno-associated virus, herpes virus (such as herpes simplex virus), poxvirus, baculovirus, papilloma virus, and papilloma vacuole virus (such as SV40). A vector may contain a variety of elements that control expression, including promoter sequences, transcription initiation sequences, enhancer sequences, selective elements, and reporter genes. In addition, the vector may also contain an origin of replication. The vector may also include components that help its entry into the cells, such as viral particles, liposomes or protein coats, but are not limited to those substances.

As used herein, the term "composition" generally refers to a composition suitable for administration to a patient. For example, the composition according to the present disclosure may comprise the immune effector cells described herein. Furthermore, the composition may also comprise one or more suitable formulations of (pharmaceutically effective) carriers, stabilizers, excipients, diluents, solubilizers, surfactants, emulsifiers and/or preservatives. Acceptable ingredients of the composition are non-toxic to the recipient at any dose and concentration used. The compositions of the present disclosure include, but are not limited to, liquids, and frozen or lyophilized compositions.

As used herein, the term "CD19" usually refers to cluster of differentiation (CD) 19 proteins, which is the cluster of antigenic determinants that can be detected on leukemia precursor cells. The amino acid and nucleic acid sequences of human and murine CD19 can be found in public databases (such as GenBank, UniProt, and Swiss-Prot). For example, the amino acid sequence of human CD19 can be accessed under UniProt/Swiss-Prot Accession Number P15391, and the nucleotide sequence encoding human CD19 can be accessed under Accession Number NM_001178098. According to the present disclosure, "CD19" may include proteins with mutations (for example, point mutations, fragments, insertions, deletions, and splice variants of full-length wild-type CD19).

As used herein, the term "subject" generally refers to a human or non-human animal, including but not limited to cat, dog, horse, pig, cow, sheep, rabbit, mouse, rat, or monkey.

As used herein, the term "lentiviral vector" generally refers to a vector comprising one or more nucleic acid sequences derived from at least part of the lentiviral genome. The lentiviral vector may comprise non-coding sequences of one or more proteins from the lentivirus.

As used herein, the term "target plasmid" may include, for example, a heterologous nucleic acid sequence (for example, a nucleic acid sequence encoding a CAR) to be transferred into a cell, and may further include, for example, one or more lentiviral genes or parts thereof.

As used herein, "helper plasmid" may contain one or more genes encoding lentiviral proteins or parts thereof. For example, a gene encoding a lentiviral capsid protein may be included, and for another example, a gene encoding an env protein or parts thereof may be included. The host cell can be transfected with a target plasmid and one or more helper plasmids to produce a virus, which can be used to infect a target cell (for example, a T cell) to express in the target cell one or more transgenes (for example, a gene encoding CAR) contained in the heterologous nucleic acid sequence.

As used herein, the term "comprising" generally refers to the inclusion of explicitly specified features, but not excluding other elements.

As used herein, the term "about" generally refers to vary within a range of 0.5%-10% greater or less than the stated value, such as varying within a range of 0.5%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5% or 10% greater or less than the stated value.

Four-Plasmid System

In one aspect, the present disclosure provides a plasmid combination, wherein the plasmid combination comprises plasmids Seq1, PMD2.G, pMDLg-pRRE and pRSV-Rev.

A four-plasmid system is used in the present disclosure to transfect lentivirus according to the method described in its instructions. The four-plasmid system may include a target plasmid (Seq1) and three helper plasmids (PMD2.G, pMDLg-pRRE and pRSV-Rev).

According to the present disclosure, the target plasmid may be Seq1. The Seq 1 carries the gene sequence of interest. The gene of interest in the vector plasmid is inserted into the genome of the target cell (293 cell) by the lentiviral vector to achieve stable expression of CAR. The transfer plasmid has an amino acid sequence shown in SEQ ID NO.1, and a nucleic acid sequence shown in SEQ ID NO.2.

Helper plasmid 1 may be PMD2.G, which is used to provide a VSV-G gene encoding vesicular stomatitis virus glycoprotein G. The VSVG-envelope-pseudotyped lentiviral vector extends the target cell tropism range of the vector and increases the stability of the lentiviral vector, thereby allowing the lentiviral vector to be concentrated by high-speed centrifugation, and further resulting in higher titer.

Helper plasmid 2 may be pMDLg-pRRE, which is used to provide a Rev protein-binding site and contains Gag and Pol genes. The Gag gene encodes major structural proteins of viral particles, such as nucleocapsid protein, membrane protein and capsid protein. The pol gene encodes viral replication-associated enzymes, such as protease, reverse transcriptase and integrase. It plays a vital role in virus assembly.

Helper plasmid 3 may be pRSV-Rev, which is used to provide a Rev gene for regulating the expression levels of the Gag and Pol genes and guiding the replication process of the single-stranded DNA, and can regulate splicing/RNA transport. It plays an important role in virus assembly.

In certain embodiments, the plasmids Seq1, PMD2.G, pMDLg-pRRE and pRSV-Rev may be present in the plasmid combination at a ratio of 2-6:1-1.5: 1-3:1-1.5, such as 2-5:1-1.5:1-3:1-1.5, 2-4:1-1.5:1-3:1-1.5, 2-3:1-1.5:1-3:1-1.5, 3-6:1-1.5:1-3:1-1.5, 3-5:1-1.5:1-3:1-1.5, 3-4:1-1.5:1-3:1-1.5, 4-6:1-1.5:1-3:1-1.5, 4-5:1-1.5:1-3:1-1.5, or 5-6:1-1.5:1-3:1-1.5. In certain embodiments, the plasmids Seq1, PMD2.G, pMDLg-pRRE and pRSV-Rev may be present at a ratio of 2-6:1-1.5:1-3:1-1.5, such as 2.1:1-1.5:1-3:1-1.5, 2.2:1-1.5:1-3:1-1.5, 2.3:1-1.5:1-3:1-1.5, 2.4:1-1.5:1-3:1-1.5, 2.5:1-1.5:1-3:1-1.5, 2.6:1-1.5:1-3:1-1.5, 2.7:1-1.5:1-3:1-1.5, 2.8:1-1.5:1-3:1-1.5, 2.9:1-1.5:1-3:1-1.5, 3.0:1-1.5:1-3:1-1.5, 3.1:1-1.5:1-3:1-1.5, 3.2:1-1.5:1-3:1-1.5, 3.3:1-1.5:1-3:1-1.5, 3.4:1-1.5:1-3:1-1.5, 3.5:1-1.5:1-3:1-1.5, 3.6:1-1.5:1-3:1-1.5, 3.7:1-1.5:1-3:1-1.5, 3.8:1-1.5:1-3:1-1.5, 3.9:1-1.5:1-3:1-1.5, 4.0:1-1.5:1-3:1-1.5, 4.1:1-1.5:1-3:1-1.5, 4.2:1-1.5:1-3:1-1.5, 4.3:1-1.5:1-3:1-1.5, 4.4:1-1.5:1-3:1-1.5, 4.5:1-1.5:1-3:1-1.5, 4.6:1-1.5:1-3:1-1.5, 4.7:1-1.5:1-3:1-1.5, 4.8:1-1.5:1-3:1-1.5, 4.9:1-1.5:1-3:1-1.5, 5.0:1-1.5:1-3:1-1.5, 5.1:1-1.5:1-3:1-1.5, 5.2:1-1.5:1-3:1-1.5, 5.3:1-1.5:1-3:1-1.5, 5.4:1-1.5:1-3:1-1.5, 5.5:1-1.5:1-3:1-1.5, 5.6:1-1.5:1-3:1-1.5, 5.7:1-1.5:1-3:1-1.5, 5.8:1-1.5:1-3:1-1.5, 5.9:1-1.5:1-3:1-1.5, or 6.0:1-1.5:1-3:1-1.5.

In certain embodiments, the plasmids Seq1, PMD2.G, pMDLg-pRRE and pRSV-Rev may be present in the plasmid combination at a ratio of 2-6:1-1.5:1-3:1-1.5, such as 2-6:1-1.3:1-3:1-1.5, 2-6:1.2-1.5:1-3:1-1.5, or 2-6:1.1-1.4:1-3:1-1.5. In certain embodiments, the plasmids Seq1, PMD2.G, pMDLg-pRRE and pRSV-Rev may be present at a ratio of 2-6:1-1.5:1-3:1-1.5, such as 2-6:1.1:1-3:1-1.5, 2-6:1.2:1-3:1-1.5, 2-6:1.3:1-3:1-1.5, 2-6:1.4:1-3:1-1.5, or 2-6:1.5:1-3:1-1.5.

In certain embodiments, the plasmids Seq1, PMD2.G, pMDLg-pRRE and pRSV-Rev may be present in the plasmid combination at a ratio of 2-6:1-1.5:1-3:1-1.5, such as 2-6:1-1.5:1-2.5:1-1.5, 2-6:1-1.5:1-2.0:1-1.5, 2-6:1-1.5:1-1.5:1-1.5, 2-6:1-1.5:1.5-3:1-1.5, 2-6:1-1.5:1.5-2.5:1-1.5, 2-6:1-1.5:1.5-2:1-1.5, 2-6:1-1.5:2-3:1-1.5, 2-6:1-1.5:2-2.5:1-1.5, or 2-6:1-1.5:2.5-3:1-1.5. In certain embodiments, the plasmids Seq1, PMD2.G, pMDLg-pRRE and pRSV-Rev may be present at a ratio of 2-6:1-1.5:1-3:1-1.5, such as 2-6:1-1.5:1.1:1-1.5, 2-6:1-1.5:1.2:1-1.5, 2-6:1-1.5:1.3:1-1.5, 2-6:1-1.5:1.4:1-1.5, 2-6:1-1.5:1.5:1-1.5, 2-6:1-1.5:1.6:1-1.5, 2-6:1-1.5:1.7:1-1.5, 2-6:1-1.5:1.8:1-1.5, 2-6:1-1.5:1.9:1-1.5, 2-6:1-1.5:2:1-1.5, 2-6:1-1.5:2.1:1-1.5, 2-6:1-1.5:2.2:1-1.5, 2-6:1-1.5:2.3:1-1.5, 2-6:1-1.5:2.4:1-1.5, 2-6:1-1.5:2.5:1-1.5, 2-6:1-1.5:2.6:1-1.5, 2-6:1-1.5:2.7:1-1.5, 2-6:1-1.5:2.8:1-1.5, 2-6:1-1.5:2.9:1-1.5, or 2-6:1-1.5:3:1-1.5.

In certain embodiments, the plasmids Seq1, PMD2.G, pMDLg-pRRE and pRSV-Rev may be present in the plasmid combination at a ratio of 11.8:3.53:6.33:2.3, 13.8:3.48:5.31:2.54 or 14:4.67:4.67:4.67. In certain embodiments, the plasmids Seq1, PMD2.G, pMDLg-pRRE and pRSV-Rev may be present at a ratio of 11.8:3.53:6.33:2.3. In certain embodiments, the plasmids Seq1, PMD2.G, pMDLg-pRRE and pRSV-Rev may be present at a ratio of 13.8:3.48:5.31:2.54. In certain embodiments, the plasmids Seq1, PMD2.G, pMDLg-pRRE and pRSV-Rev may be present at a ratio of 14:4.67:4.67:4.67.

Chimeric Antigen Receptor, Nucleic Acid, Vector, Immune Effector Cell, and Composition The plasmid Seq1 of the present disclosure can express a chimeric antigen receptor, comprising the amino acid sequence shown in SEQ ID NO.1. The present disclosure further provides a chimeric antigen receptor, comprising an amino acid sequence having at least 80% (such as at least 80%, at least 85%, at least 90%, at least 91%, at least 92%, at least 93%, at least 94%, at least 95%, at least 96%, at least 97%, at least 98%, or at least 99%) sequence identity with the amino acid sequence shown in SEQ ID NO. 1.

In certain embodiments, the chimeric antigen receptor described herein can specifically bind to and/or recognize tumor antigens. For example, the chimeric antigen receptor described herein can specifically bind to and/or recognize CD19 antigen.

In certain embodiments, the chimeric antigen receptor described herein can promote an immune effector cell to secrete cytokine. The immune effector cell may be selected from the group consisting of T lymphocytes and natural killer cells. The cytokine may be selected from the group consisting of IFN-γ and IL-6. The immune effector cell may be a mammalian immune effector cell. The T lymphocyte may be a mammalian T lymphocyte, and the natural killer cell may also be a mammalian natural killer cell. The T lymphocyte may be a human T lymphocyte, and the natural killer cell may also be a human natural killer cell.

In certain embodiments, the chimeric antigen receptor described herein is non-hemolytic and vascular irritation-free.

In certain embodiments, the chimeric antigen receptor described herein is non-oncogenic in vitro.

In certain embodiments, the chimeric antigen receptor described herein is non-oncogenic in vivo.

In certain embodiments, the chimeric antigen receptor described herein can effectively treat tumors. The tumor may be a CD19-positive tumor. For example, the chimeric antigen receptor described herein can effectively prolong the survival time of patients with CD19-positive tumors. For example, the chimeric antigen receptor described herein can effectively prolong the survival time of patients with non-solid tumors. For example, the chimeric antigen receptor described herein can effectively prolong the survival time of lymphoma and/or leukemia. For another example, the chimeric antigen receptor described herein can effectively prolong the survival time of adult patients with acute lymphoblastic leukemia. For another example, the chimeric antigen receptor described herein can effectively prolong the survival time of children patients with acute lymphoblastic leukemia. For another example, the chimeric antigen receptor described herein can effectively prolong the survival time of patients with B-cell lymphoma (for example, non-Hodgkin's lymphoma).

In certain embodiments, the chimeric antigen receptor described herein can effectively treat acute lymphoblastic leukemia in adults.

In certain embodiments, the chimeric antigen receptor described herein can effectively treat acute lymphoblastic leukemia in children.

In certain embodiments, the chimeric antigen receptor described herein can effectively treat non-Hodgkin's lymphoma.

The plasmid Seq1 of the present disclosure comprises an isolated nucleic acid molecule encoding the chimeric antigen receptor described herein.

The plasmid Seq1 of the present disclosure comprises an isolated nucleic acid molecule encoding a chimeric antigen receptor, wherein the nucleic acid molecule comprises the nucleic acid sequence shown in SEQ ID NO.2.

The plasmid Seq1 of the present disclosure comprises an isolated nucleic acid molecule encoding a chimeric antigen receptor, wherein the nucleic acid molecule comprises a nucleic acid sequence analogous to the sequence shown in SEQ ID NO.2 and is a nucleic acid molecule encoding the chimeric antigen receptor.

In certain embodiments, the nucleic acid sequence analogous to the sequence shown in SEQ ID NO.2 refers to a nucleic acid sequence having at least 70%, 75%, 80%, 85%, 90%, 95%, 96%, 97%, 98%, or 99% sequence identity with the nucleic acid sequence shown in SEQ ID NO. 2.

In certain embodiments, the nucleic acid sequence analogous to the sequence shown in SEQ ID NO.2 means that the nucleic acid molecule can encode the chimeric antigen receptor, though it is different from the nucleic acid sequence shown in SEQ ID NO. 2 owing to the wobble (degeneracy) of the base at position 3 of the nucleic acid codon.

The present disclosure includes variants of genes and proteins (for example, variants of the amino acid sequence shown in SEQ ID NO.1, or variants of the nucleic acid sequence shown in SEQ ID NO. 2 as described herein), which retain one or more biological activities. Such variants of the protein or polypeptide include a protein or polypeptide that has been or can be modified using recombinant DNA technology so that the protein or polypeptide has altered or additional properties; for example, the variant confers enhanced stability in plasma or increased activity to the protein. The variant may be different from the reference sequence, e.g., being different from a naturally occurring polynucleotide, protein or peptide. At the nucleotide sequence level, the naturally occurring variant gene and the non-naturally occurring variant gene will typically have at least about 50%, more typically at least about 70%, and even more typically at least about 80% identity (90% or higher identity) to the reference gene. At the amino acid sequence level, the naturally occurring variant protein and the non-naturally occurring variant protein will typically have at least about 70%, more typically at least about 80%, and even more typically at least about 90% or higher identity to the reference protein, while allowing higher percent non-identity regions in non-conserved regions (e.g., the percent identity being less than 70%, such as less than 60%, less than 50%, or even less than 40%). In other embodiments, the sequence has at least 60%, 70%, 75% or more identity (e.g., 80%, 85%, 90%, 95%, 96%, 97%, 98%, 99% or higher identity) with the reference sequence. The modification procedures for introducing a nucleotide and an amino acid into a polynucleotide, protein, or polypeptide have been known to those skilled in the art (see, for example, Sambrook et al. (1989)).

As used herein, the term "identity", "homology" and their grammatical variants generally mean that two or more entities are identical when their sequences are "aligned". Thus, for example, when two polypeptides have identical sequences, they have the same amino acid sequence at least within the reference regions or parts. If two polynucleotides have identical sequences, they have the same polynucleotide sequence at least within the reference regions or parts. The identity can be the identity of the defined zones (regions or domains) of the sequences. The "zones" or "regions" of identity refer to the same parts of two or more reference entities. Therefore, if two proteins or nucleic acid sequences are the same in one or more sequence zones or regions, they have identity in that region. "Aligned" sequences refer to more polynucleotide or protein (amino acid) sequences, which often contain supplementary or additional bases or amino acids (gaps) compared with the reference sequence. The degree of identity (homology) between two sequences can be determined using computer programs and mathematical algorithms Such algorithms that calculate percent sequence identity (homology) generally calculate sequence gaps and mismatches in the compared regions or zones. For example, BLAST (for example, BLAST 2.0) search algorithm (see, for example, Altschul et al., J. Mol. Biol. 215: 403 (1990), publicly available from NCBI) gives exemplary search parameters as follows: Mismatch-2, gap opening 5, gap extension 2.

According to the present disclosure, the nucleic acid molecule may be a nucleotide, deoxyribonucleotide or ribonucleotide of any length in its isolated form, or an analog that has been isolated from their natural environment or artificially synthesized, as long as it is capable of encoding the chimeric antigen receptor described herein.

In another aspect, the present disclosure provides a vector comprising the nucleic acid molecule described herein.

According to the present disclosure, the vector can be transformed, transduced or transfected into the host cell so that the genetic material element it carries can be expressed in the host cell. For example, vectors include a plasmid; a phagemid; a cosmid; an artificial chromosome (such as yeast artificial chromosome (YAC), a bacterial artificial chromosome (BAC) or a P1-derived artificial chromosome (PAC)); a phage such as λ phage or M13 phage and an animal virus, etc. The types of animal viruses as the vector include retrovirus (including lentivirus), adenovirus, adeno-associated virus, herpes virus (such as herpes simplex virus), poxvirus, baculovirus, papilloma virus, and papilloma vacuole virus (such as SV40). For another example, the vector may contain a variety of elements that control expression, including promoter sequences, transcription initiation sequences, enhancer sequences, selective elements, and reporter genes. In addition, the vector may also contain an origin of replication. Moreover, the vector may also include components that help its entry into the cells, such as viral particles, liposomes or protein coats, but are not limited to those substances.

In one aspect, the present disclosure provides a method for preparing a lentiviral vector, the method comprising introducing the plasmid combination into a cell.

In another aspect, the present disclosure provides an immune effector cell, comprising the chimeric antigen receptor, the nucleic acid molecule and/or the vector described herein. According to the present disclosure, the immune effector cell may be selected from the group consisting of T lymphocytes and natural killer cells. In certain embodiments, the immune effector cell may be a human immune effector cell. For example, the immune effector cell can be a human T lymphocyte. For another example, the immune effector cell can be a human natural killer cell.

According to the present disclosure, the chimeric antigen receptor described herein is expressed on the surface of the immune effector cell.

In certain embodiments, the immune effector cell described herein can effectively kill tumor cells. The tumor cells may be CD19-positive cells. For example, the immune effector cell described herein can considerably lower the residual rate of CD19-positive human leukemia cell line Nalm-6 cells.

In certain embodiments, the immune effector cell described herein can effectively promote cytokine secretion when it comes into contact with CD19-positive cells. The cytokine may be selected from the group consisting of IFN-γ and IL-6. For example, co-culturing the immune effector cell described herein with CD19-positive human leukemia cell line Nalm-6 cells results in a significant increase in the secretion of IFN-γ and IL-6 cytokine.

In certain embodiments, the immune effector cell described herein is non-hemolytic and vascular irritation-free. For example, in hemolysis test in vitro, the immune effector cell described herein would not induce hemolysis and blood aggregation. For another example, the immune effector cell described herein is vascular irritation-free.

In certain embodiments, the immune effector cell described herein is non-oncogenic in vitro.

In certain embodiments, the immune effector cell described herein is non-oncogenic in vivo.

In certain embodiments, the immune effector cell described herein can effectively treat tumors. The tumor may be a CD19-positive tumor. For example, the immune effector cell described herein can effectively prolong the survival time of patients with CD19-positive tumors. For another example, the immune effector cell described herein can effectively prolong the survival time of adult patients with acute lymphoblastic leukemia. For another example, the immune effector cell described herein can effectively prolong the survival time of children patients with acute lymphoblastic leukemia. For another example, the immune effector cell described herein can effectively prolong the survival time of patients with B-cell lymphoma (such as non-Hodgkin's lymphoma).

In certain embodiments, the immune effector cell described herein can effectively treat acute lymphoblastic leukemia in adults.

In certain embodiments, the immune effector cell described herein can effectively treat acute lymphoblastic leukemia in children.

In certain embodiments, the immune effector cell described herein can effectively treat B-cell lymphoma (such as non-Hodgkin's lymphoma).

In another aspect, the present disclosure provides a composition comprising the immune effector cell described herein.

According to the present disclosure, the composition may also comprise one or more suitable formulations of (pharmaceutically effective) carriers, stabilizers, excipients, diluents, solubilizers, surfactants, emulsifiers and/or preservatives. Acceptable ingredients of the composition are non-toxic to the recipient at any dose and concentration used. The compositions of the present disclosure include, but are not limited to, liquids, and frozen or lyophilized compositions.

In certain embodiments, the composition may be a composition for parenteral, transdermal, intraluminal, intraarterial, intrathecal and/or intranasal administration or by direct injection into tissue. For example, the composition may be administered to a patient or subject via infusion or injection. In other embodiments, administration of the composition may be effected by different ways, e.g., by intravenous, intraperitoneal, subcutaneous, intramuscular, topical or intradermal administration. In other embodiments, the composition can be administered uninterruptedly. The uninterrupted (or continuous) administration may be realized by a small pump system worn by the patient for metering the influx of therapeutic agent into the body of the patient, as described in WO2015/036583.

According to the present disclosure, the dosage regimen of the composition may be a dose of a rapid infusion agent, multiple divided doses administered over time, or the doses may be decreased or increased in proportion to the severity and urgency of the treatment situation. In certain embodiments, the treatment regimen can be administered once a week, once every two weeks, once every three weeks, once every four weeks, once a month, once every three months, or once every three to six months. In certain embodiments, the dosage regimen includes intravenous administration, and the dose may be administered in a range of $0.1 \times 10^8$ to $3 \times 10^8$ CAR-positive T cells, for example, $0.15 \times 10^8$ to $2 \times 10^8$ CAR-positive T cells, $0.5 \times 10^8$ to $2 \times 10^8$ CAR-positive T cells, $1 \times 10^8$ to $2 \times 10^8$ CAR-positive T cells, $0.2 \times 10^8$ to $2 \times 10^8$ CAR-positive T cells, $0.2 \times 10^8$ to $1 \times 10^8$ CAR-positive T cells, $0.25 \times 10^8$ to $1 \times 10^8$ CAR-positive T cells, $0.25 \times 10^8$ to $0.5 \times 10^8$ CAR-positive T cells, or $0.5 \times 10^8$ CAR-positive T cells, or $2 \times 10^8$ CAR-positive T cells.

The doses for administration may vary for different indications. In certain embodiments, the immune effector cell for the treatment of adult patients with relapsed and refractory acute lymphoblastic leukemia may be administered at a dose of $0.25 \times 10^8$ to $0.5 \times 10^8$ CAR-positive T cells, or $0.5 \times 10^8$ CAR-positive T cells, e.g., $0.3 \times 10^8$ to $0.5 \times 10^8$, $0.4 \times 10^8$ to $0.5 \times 10^8$, $0.25 \times 10^8$ to $0.4 \times 10^8$, $0.3 \times 10^8$ to $0.4 \times 10^8$, or $0.4 \times 10^8$ to $0.5 \times 10^8$ CAR-positive T cells. In certain embodiments, the immune effector cell for the treatment of adult patients with relapsed and refractory acute lymphoblastic leukemia may be administered at a dose of $0.25 \times 10^8$, $0.26 \times 10^8$, $0.27 \times 10^8$, $0.28 \times 10^8$, $0.29 \times 10^8$, $0.3 \times 10^8$, $0.31 \times 10^8$, $0.32 \times 10^8$, $0.33 \times 10^8$, $0.34 \times 10^8$, $0.35 \times 10^8$, $0.36 \times 10^8$, $0.37 \times 10^8$, $0.38 \times 10^8$, $0.39 \times 10^8$, $0.4 \times 10^8$, $0.41 \times 10^8$, $0.42 \times 10^8$, $0.43 \times 10^8$, $0.44 \times 10^8$, $0.45 \times 10^8$, $0.46 \times 10^8$, $0.47 \times 10^8$, $0.48 \times 10^8$, $0.49 \times 10^8$ or $0.5 \times 10^8$ CAR-positive T cells.

In certain embodiments, the immune effector cell for the treatment of children patients with relapsed and refractory acute lymphoblastic leukemia may be administered at a dose of $0.25 \times 10^8$ to $0.5 \times 10^8$ CAR-positive T cells, or $0.5 \times 10^8$ CAR-positive T cells, e.g., $0.3 \times 10^8$ to $0.5 \times 10^8$, $0.4 \times 10^8$ to $0.5 \times 10^8$, $0.25 \times 10^8$ to $0.4 \times 10^8$, $0.3 \times 10^8$ to $0.4 \times 10^8$, or $0.4 \times 10^8$ to $0.5 \times 10^8$ CAR-positive T cells. In some embodiments, the immune effector cell for the treatment of children patients with relapsed and refractory acute lymphoblastic leukemia may be administered at a dose of $0.25 \times 10^8$, $0.26 \times 10^8$, $0.27 \times 10^8$, $0.28 \times 10^8$, $0.29 \times 10^8$, $0.3 \times 10^8$, $0.31 \times 10^8$, $0.32 \times 10^8$, $0.33 \times 10^8$, $0.34 \times 10^8$, $0.35 \times 10^8$, $0.36 \times 10^8$, $0.37 \times 10^8$, $0.38 \times 10^8$, $0.39 \times 10^8$, $0.4 \times 10^8$, $0.41 \times 10^8$, $0.42 \times 10^8$, $0.43 \times 10^8$, $0.44 \times 10^8$, $0.45 \times 10^8$, $0.46 \times 10^8$, $0.47 \times 10^8$, $0.48 \times 10^8$, $0.49 \times 10^8$ or $0.5 \times 10^8$ CAR-positive T cells.

In other embodiments, the immune effector cell for the treatment of patients with relapsed and refractory non-Hodgkin's lymphoma may be administered at a dose of $1 \times 10^8$ to $2 \times 10^8$ CAR-positive T cells, or $2 \times 10^8$ CAR-positive T cells, e.g., $1 \times 10^8$ to $1.8 \times 10^8$, $1 \times 10^8$ to $1.5 \times 10^8$, $1 \times 10^8$ to $1.3 \times 10^8$, $1.3 \times 10^8$ to $2 \times 10^8$, $1.3 \times 10^8$ to $1.5 \times 10^8$, $1.5 \times 10^8$ to $2 \times 10^8$, $1.5 \times 10^8$ to $1.8 \times 10^8$ or $1.8 \times 10^8$ to $2 \times 10^8$ CAR-positive T cells. In other embodiments, the immune effector cell for the treatment of patients with relapsed and refractory Hodgkin's lymphoma may be administered at a dose of $1 \times 10^8$, $1.1 \times 10^8$, $1.2 \times 10^8$, $1.3 \times 10^8$, $1.4 \times 10^8$, $1.5 \times 10^8$, $1.6 \times 10^8$, $1.7 \times 10^8$, $1.8 \times 10^8$, $1.9 \times 10^8$ or $2.0 \times 10^8$ CAR-positive T cells.

Preparation Method and Use

In another aspect, the present disclosure further provides a method for preparing an immune effector cell, comprising a step of transducing the plasmid or vector described herein into the immune effector cell.

In certain embodiments, the immune effector cell is selected from the group consisting of T lymphocytes and natural killer cells.

In another aspect, the present disclosure further provides use of the chimeric antigen receptor, the nucleic acid molecule, the vector and/or the immune effector cell in the manufacture of a medicament, wherein the medicament is useful for treating a disease or disorder associated with CD19 expression. The doses of the medicament for administration may refer to those defined for the immune effector cell as mentioned above.

In another aspect, the present disclosure further provides a method for treating a disease or disorder associated with CD19 expression, comprising applying the chimeric antigen receptor, the nucleic acid molecule, the vector and/or the immune effector cell described herein to a subject in need thereof. According to the present disclosure, the administration of the composition may be effected by different ways, e.g., by intravenous, intratumor, intraperitoneal, subcutaneous, intramuscular, topical or intradermal administration.

In another aspect, the chimeric antigen receptor, the nucleic acid molecule, the vector and/or the immune effector cell described herein is useful for the treatment of a disease or disorder associated with CD19 expression.

According to the present disclosure, the medicament may include T-cell immunotherapy agents.

According to the present disclosure, the disease or disorder associated with CD19 expression may include non-solid tumors.

According to the present disclosure, the disease or disorder associated with CD19 expression may include leukemia and/or lymphoma.

In certain embodiments, the disease or disorder associated with CD19 expression may comprise acute lymphoblastic leukemia (ALL), such as adult acute lymphoblastic leukemia (ALL) and/or childhood acute lymphoblastic leukemia (ALL).

In other embodiments, the disease or disorder associated with CD19 expression may comprise adult chronic lymphocytic leukemia (CLL). In other embodiments, the disease or disorder associated with CD19 expression may comprise B-cell lymphoma. For example, the B-cell lymphoma may comprise non-Hodgkin's lymphoma.

According to the present disclosure, the subject may comprise a human or non-human animal. For example, the subject can include, but not limited to, cat, dog, horse, pig, cow, sheep, rabbit, mouse, rat, or monkey.

Without wishing to be bound by any theory, the following examples are only described to illustrate the chimeric antigen receptor, the immune effector cell, the preparation method and use of the present disclosure, and are not used to limit the scope thereof. The examples do not include detailed descriptions of traditional methods, such as those used to construct vectors and plasmids, methods of inserting genes encoding proteins into such vectors and plasmids, or methods of introducing plasmids into host cells. Such methods have been well-known to those of ordinary skill in the art, and described in many publications, including Sambrook, J., Fritsch, E. F. and Maniais, T. (1989) Molecular Cloning: A Laboratory Manual, 2nd edition, Cold spring Harbor Laboratory Press.

All patents, applications and references cited in this disclosure are incorporated herein by reference in their entirety, to the extent that each document is cited for reference individually. If any material incorporated by reference contradicts or is inconsistent with this description, the description will supersede any of such materials.

EXAMPLES

Example 1

Construction and Preparation of a Lentiviral Vector

A fragment containing the CAR structure described in the present disclosure (its amino acid sequence and nucleotide sequence are shown in SEQ ID NO. 1 and SEQ ID NO. 2, respectively) was artificially synthesized, and constructed into a modified empty vector (manufacturer: SBI Corporation, catalog number: CD500-CD800). Three helper plasmids were used for packaging to obtain a lentiviral vector, and the obtained lentiviral vector was named the expression vector CNCT19. The specific steps are described as follows.

1.1 Construction of a Plasmid Vector

In the present disclosure, a four-plasmid system containing a target plasmid (Seq1), PMD2.G, pMDLg-pRRE and pRSV-Rev was used.

Firstly, the target plasmid Seq1 was constructed. An empty vector (manufacturer: SBI System BioScience; name: PCDH-EF1-MCS-T2A-copGFP; catalog number: CD526A-1) was cleaved with the two restriction enzymes Nhe I (GCTAGC) and Not I (GCGGCCGC), and was connected to the CAR gene fragment which contained Nhe I and Not I enzyme-digested sequences at both ends and encoded the amino acid sequence shown in SEQ ID NO:1, and the GFP sequence was removed to obtain the vector ①. The vector ① was cleaved with the two restriction enzymes Not I (GCGGCCGC) and Sal I (GTCGAC), and the T2A sequence was removed. The sticky ends were made blunt with the Klenow Fragment enzyme, and solution I ligase was added for ligation to obtain the vector ②. A PCR method was performed to amplify the sequence of the vector ② except the ampicillin resistance (AmpR) genes, and amplify the synthetic kanamycin resistance (KanR) gene, and then the two fragments was ligated with a recombinase to obtain the target plasmid Seq1 which contained the nucleotide sequence shown in SEQ ID NO: 2.

After that, three helper plasmids were prepared, wherein helper plasmid 1 was PMD2.G (purchased from Biovector, with a product number of Biovector 12259); helper plasmid 2 was pMDLg-pRRE (purchased from Biovector Corporation, with a product number of Biovector012251); and helper plasmid 3 was pRSV-Rev (purchased from Biovector Corporation, with a product number of Biovector012253).

The four plasmids, Seq1, PMD2.G, pMDLg-pRRE and pRSV-Rev, were used for packaging in the following different four plasmid ratios:

ratio 1 of Seq1:PMD2.G:pMDLg-pRRE:pRSV-Rev was 11.8:3.53:6.33:2.3;

ratio 2 of Seq1:PMD2.G:pMDLg-pRRE:pRSV-Rev was 13.8:3.48:5.31:2.54;

ratio 3 of Seq1:PMD2.G:pMDLg-pRRE:pRSV-Rev was 14:4.67:4.67:4.67;

ratio 4 of Seq1:PMD2.G:pMDLg-pRRE:pRSV-Rev was 2:1:1:1;

ratio 5 of Seq1:PMD2.G:pMDLg-pRRE:pRSV-Rev was 7:3:5:5;

ratio 6 of Seq1:PMD2.G:pMDLg-pRRE:pRSV-Rev was 9:3:4:6; and in the comparative example, the ratio of Seq1:PsPAX2:PMD2.G was 14:10.5:3.5.

1.2 Preparation of a Lentiviral Vector (1) Recovery of cells: cryopreserved 293T/17 cells were recovered and the recovered cells were cultured at 37° C. with 5% $CO_2$;

(2) Subculture of cells: the recovered cells were subcultured in T175 culture flasks until the cell growth density reached 85-95% of the bottom of the flask;

(3) Cell pretreatment: the cells were added to a 10 cm-culture dish at $5\times10^6$ cells/dish, and cultured at 37° C. with 5% $CO_2$;

(4) Preparation of a packaging system: 2 ml of DMEM was taken, the target plasmid and three helper plasmids were added in a specific ratio to form a four-plasmid system, 28 μl of PEI was added, and the mixture was thoroughly mixed and allowed to stand at room temperature for 15 min;

(5) Plasmid transfection: cells were pretreated and cultured until the cell growth density reached 60-90% of the bottom of the dish, and the prepared solution of the packaging system was transferred to the culture dish for transfection; the transfection was carried out at 37° C., with 5% $CO_2$;

(6) Collection of viruses: 16-18 h after transfection, the medium was changed with an equal volume of DMEM containing 10% FBS and the incubation was continued for 24 hours before the virus liquid was collected for the first time, then the medium was changed and an equal volume of DMEM containing 10% FBS was added, and another 24 hours of incubation was performed before the virus liquid was collected for the second time, wherein the incubation was performed at 37° C. with 5% $CO_2$.

(7) Clarification of the virus liquid: the lentiviral vector liquid was centrifuged at 19° C. at 3000 rpm for 15 min, the precipitate was discarded, and supernatant was obtained;

(8) Concentration of viruses: the supernatant was filtered with a 0.45 μm filter to a high-speed centrifuge tube and centrifuged at a high speed of 50,000 g at 4° C. for 90 min, the supernatant was discarded, the precipitate was dissolved in lymphocyte culture medium before being stored in a low-temperature refrigerator at −80° C. for later use, and a lentiviral vector packaged by a four-plasmid system was obtained and named CNCT19 lentiviral vector.

1.3 Determination of Physical Titer and Transfection Titer

The concentrated virus solution was taken at 210 μl/tube, the physical titer was determined using ELISA, and the transfection titer was detected using a flow cytometer. The physical titer indicates the number of lentiviral particles. The transfection titer represents the number of active lentiviral particles.

Figure 1B:
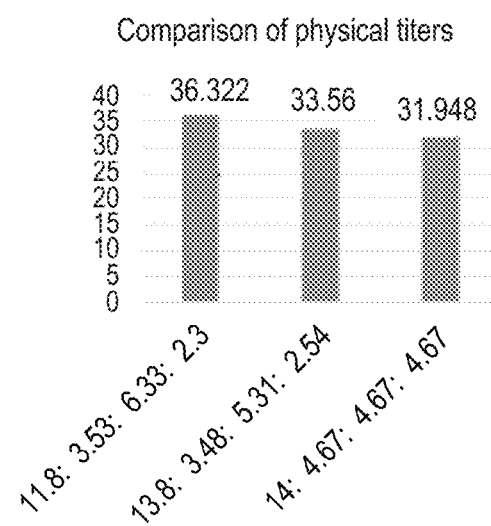
FIG. 1B shows the physical titer after the transfection with the four-plasmid system.

The test results are shown in Table 1 and Table 2, and FIG. 1A and FIG. 1B. The results of Table 1, FIG. 1A and FIG. 1B show that configuration of the lentivirus packaging systems in the quality ratios of the four plasmids (Seq1:PMD2.G:pMDLg-pRRE:pRSV-Rev) of 11.8:3.53:6.33:2.3, 13.8:3.48:5.31:2.54 and 14:4.67:4.67:4.67 resulted in almost the same packaging efficiency and all led to higher transfection titer than the comparative example. Table 2 shows that the quality ratios of the four plasmids (Seq1:PMD2.G:pMDLg-pRRE:pRSV-Rev) of 7:3:5:5 and 9:3:4:6 led to significantly higher transfection titer than ratio 4 and the ratio of the comparative example, with the transfection titer reaching two times more than that resulting from ratio 4 and the ratio of the comparative example. The results show that the transfection titer resulting from ratios 1, 2 and 3 was higher than that resulting from ratios 4, 5 and 6 and the ratio of the comparative example, wherein the transfection titer resulting from ratios 1, 2 and 3 was two times more than that resulting from ratio 4 and the ratio of the comparative example.

TABLE 1

The transfection titer and the physical titer resulting from ratios 1, 2 and 3

| No. | Quality ratios of the plasmids Seq1:PMD2.G:pMDLg-pRRE:pRSV-Rev | Transfection titer | Physical titer |
|---|---|---|---|
| Ratio 1 | 11.8:3.53:6.33:2.3 | 4.2E+07 | 36.322 |
| Ratio 2 | 13.8:3.48:5.31:2.54 | 3.59E+07 | 33.56 |
| Ratio 3 | 14:4.67:4.67:4.67 | 4.03E+07 | 31.948 |

TABLE 2

The transfection titer and the physical titer resulting from ratios 4, 5, 6 and 7 and the ratio of the comparative example

| No. | Quality ratios of the plasmids Seq1:PMD2.G:pMDLg-pRRE:pRSV-Rev | Transfection titer |
|---|---|---|
| Ratio 4 | 2:1:1:1 | 1.47E+07 |
| Ratio 5 | 7:3:5:5 | 3.18E+07 |
| Ratio 6 | 9:3:4:6 | 3.33E+07 |
| Ratio of the comparative example | (Seq1:PsPAX2:PMD2.G) 14:10.5:3.5 | 1.37E+07 |

Example 2

Preparation of T Cells Infected with Lentiviruses

The infection experiment was carried out according to conventional methods known to those skilled in the art. The steps of infection are briefly described as follows:

1. Sorting of T Cells

Peripheral blood mononuclear cells (PBMC) were isolated from the subject's apheresis cells, and then T cells were sorted from the PBMC cells.

2. Activation of the T Cells

The isolated T cells were resuspended with complete lymphocyte culture medium (Xvivo15 medium+5% FBS+100 IU/ml IL-2 or Xvivo15 medium+5% FBS+20 ng/ml IL-21+10 ng/ml IL-7) to give a final concentration of $(1\sim2)\times10^6$ cells/ml, and 5 to 10 µl of CD3/CD28 stimulation magnetic beads were added. The mixture was well mixed, and placed in an incubator for culture for at least 24 h under the culture condition of 37° C.+5% $CO_2$.

3. Infection of T Cells with Lentiviruses

The activated cultured T cells were taken out, and polybrene at a final concentration of 8 µg/ml was added and mixed well. The CNCT19 lentiviral vector obtained in Example 1 was slowly added at MOI=2. After well mixed, the mixture was placed in a centrifuge and centrifuged at 1500 rpm for 1.5 h. After that, it was placed in an incubator for culture for at least 24 h under the culture condition of 37° C.+5% $CO_2$.

4. Expansion Culture of Infected T Cells

The infected cells were taken out and the cell density was monitored to keep it at $(0.5\sim1)\times10^6$ cells/ml for use in subsequent examples. The obtained infected T cells were named CNCT19 cells (i.e., the immune effector cells described herein).

Example 3

Detection of the Expression of CAR Molecules on the Surface of CNCT19 Cells

The steps of the experiment are as follows:

(1) The CNCT19 cell suspension was centrifuged at 300 g for 5 min, the supernatant was discarded, sheath fluid was added to resuspend until the viable cell density reached $(0.5\sim1)\times10^7$ cells/ml.

(2) Two flow cytometry tubes were taken for each sample, and labeled Tube 1 and Tube 2; Tube 1 was a blank control and there was no need to add antibodies to it, and to Tube 2 was added 10 µL of a ten-fold dilution of Alexa Fluor® 647-goat anti-mouse IgG F(ab')$_2$ antibody (manufacturer: Jackson, catalog number: 115-605-072).

(3) To each tube was added 100 µl of cell suspension, and reaction was performed for 15 to 20 min in the dark at room temperature.

(4) To each tube was added 2 ml of sheath fluid for washing, and centrifugation was performed at 300 g for 5 min.

(5) The supernatant was discarded, and 20 µl of FITC-CD3 (manufacturer: Tongsheng Shidai, catalog number: Z6410047-100T) was added to Tube 2, and incubated for 15 to 20 min in the dark at room temperature.

(6) To each tube was added 2 ml of sheath fluid for washing, centrifugation was performed at 300 g for 5 min, the supernatant was discarded, an additional 2 ml of sheath fluid was added to each tube for washing, and centrifugation was performed at 300 g for 5 min.

(7) The supernatant was discarded, and after resuspension was performed by adding 300 µl of sheath fluid to each tube, detection was performed by flow cytometry.

Figure 2A:
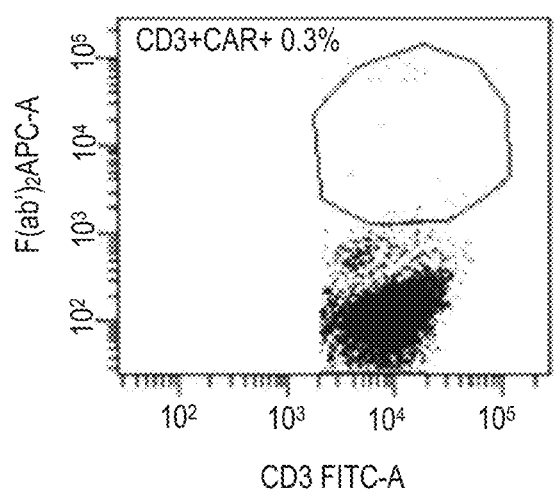
FIG. 2A shows the detection results of CAR molecules expressed on the surface of CNCT19 cells.
Figure 2B:
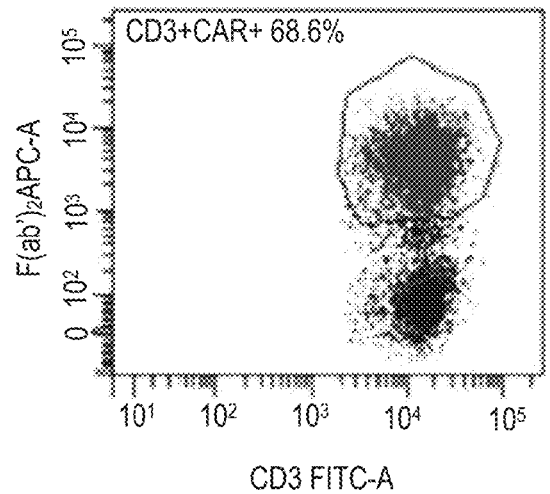
FIG. 2B shows the detection results of CAR molecules expressed on the surface of CNCT19 cells.

The results are presented in FIG. 2A and FIG. 2B. As can be seen, FIG. 2A represents a blank control tube; its upper-right CD3+CAR+quadrant shows no cell population. FIG. 2B represents an experimental detection tube. CART cells were labeled with IgG F(ab')$_2$ and CD3 antibodies and a CAR expression rate of 68.6% can be clearly detected in the CD3$^+$CAR+ quadrant by flow cytometry. The results indicate that the CAR molecules according to the present disclosure are well expressed on the surface of CNCT19 cells.

Example 4

Detection of the Killing Effect of CNCT19 Cells on Target Cells In Vitro

The experimental steps of this example are as follows:

1) The CD19-positive human leukemia cell line Nalm-6 (purchased from Shanghai Enzyme Research Bioscience Co., Ltd., catalog number: CH179) and the CD19-negative human leukemia cell line KG-1a (purchased from Shanghai Enzyme Research Bioscience Co., Ltd., catalog number: CC-Y1305) were respectively selected as the tumor cells (i.e., target cells). CD19 CAR-T cells (i.e., CNCT19 cells obtained in Example 2) and untransfected T cells (denoted by NTD) were respectively selected as the effector cells.

2) The aforementioned target cells and effector cells were mixed at effector/target ratios of 1:2 and 2:1 respectively and seeded in a 24-well plate. The total number of the cells co-cultured in each well was made to be about $1\times10^6$/well, and three parallel wells were set for each condition. Each well was replenished with culture solution to 1 ml, the plate was placed in an incubator at 37° C. with 5% $CO_2$ for culture, and the time was recorded.

3) After 24 hours of co-culture, cell suspension in each well was collected, transferred to 1.5 mL EP tubes, and labeled respectively. In addition, after centrifugation, the supernatant from each sample tube was sucked into a new 1.5 mL EP tube, and cryopreserved at −20° C. for subsequent cytokine detection (see Example 6 for details).

4) According to the type of the tumor cells, a corresponding detection amount of antibodies were respectively added to the mixed cells in each well for labeling, and an operation was performed according to the antibody instruction. PE-CD10 antibodies were used to label Nalm-6 cells, and Percp-cy5.5-CD45 antibodies were used to label KG-1a cells.

5) Flow cytometry was used to detect the change in the proportion of different target tumor cells in each sample.

Figure 3:
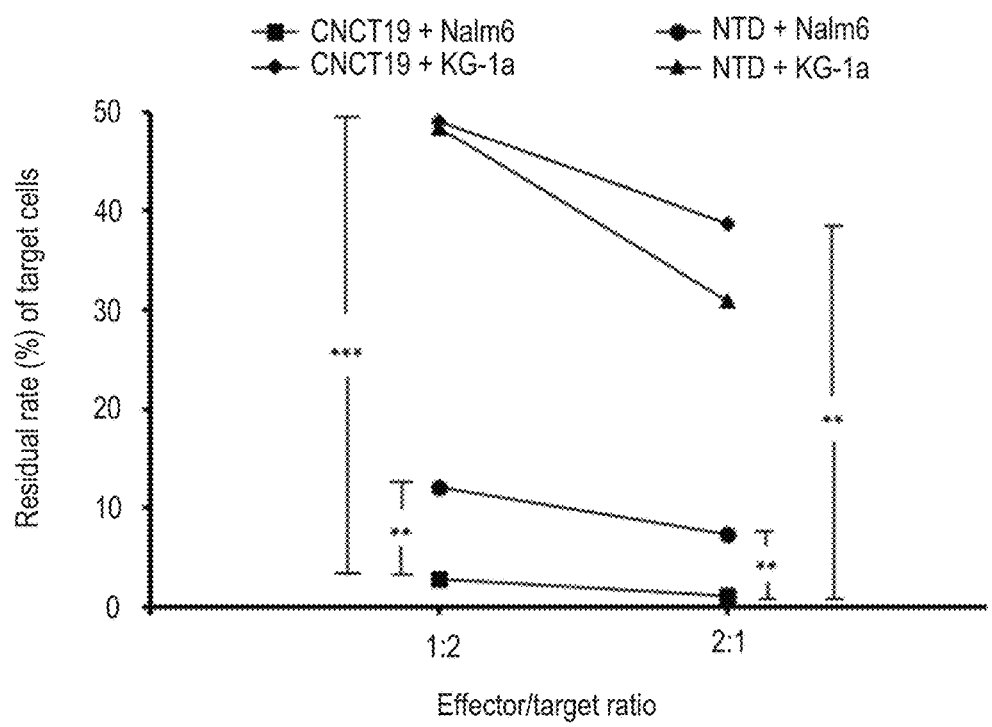
FIG. 3 shows residual rates of tumor cells under different co-culture conditions.

The results are shown in FIG. 3. As can be seen, compared with the co-culture with untransfected T cells (i.e., NTD), co-culture of the CD19-positive tumor cells Nalm-6 with CAR-T cells (i.e., CNCT19 cells) led to a significantly reduced residual rate of Nalm-6; nevertheless, there was no significant difference in the residual rates of KG-1a after the CD19 negative tumor cells KG-1a were co-cultured with various effector cells. Specifically, where the effector/target ratio was 1:2, co-incubation of CNCT19 cells with Nalm-6 cells led to a residual rate of target cells of (2.8±1.3)%, which was significantly lower than that ((12.1±1.2)% ($P<0.01$)) resulting from co-incubation of untransfected T cells with Nalm-6 cells. Likely, where the effector/target ratio was 2:1, co-incubation of CNCT19 cells with Nalm-6 cells led to a residual rate of target cells of (1.1±0.1)%, which was significantly lower than that ((7.3±1.2)% ($P<0.01$)) resulting from co-incubation of untransfected T cells with Nalm-6 cells. Moreover, the killing effect of CNCT19 cells on CD19-positive tumor cells enhanced with the increase of the effector/target ratio.

Example 5

Real-Time Monitoring of the Killing Function of CNCT19 Cells

The experimental steps are as follows:

(1) The target cells CHO-CD19 were taken out, the culture solution in the culture flask was aspirated and discarded, the culture flask was washed once with physiological saline solution, 1 ml of trypsin solution containing EDTA was added, and incubation was performed in a 37° C. incubator for 2 to 6 min before the digestion was stopped. It should be noted that the CHO cells were purchased from Shanghai Enzyme Research Bioscience Co., Ltd., with a catalog number of CC-Y2110; the molecular sequences of CD19 cells were derived from NCBI, and the molecular sequences of CD19 were constructed into the CHO cells by a method of molecular biology, and the target cells CHO-CD19 cell strains were obtained through screening.

(2) An appropriate amount of culture medium was added to the culture flask to make the target cells form a cell suspension, and the cells were made uniform by pipetting. After the concentration of the cell suspension was counted with a counting plate, the cell suspension was formulated to a cell concentration of $1\times10^5$ cells/ml as required by the experiments.

(3) 50 µl of culture medium was added to the wells of E-Plate 16 of the RTCA DP system. E-Plate 16 was placed on the RTCA Station. The RTCA system would automatically scan ("Scan Plate") to check whether the contact was good ("Connection OK" was displayed on the "Message" page). Detection of the baseline (Background) was started to make sure that the selected well was in normal contact.

(4) E-Plate 16 was taken out, and 100 µl of well-mixed target cell suspension was added to the wells at $1\times10^4$ cells per well. The E-Plate 16 was placed in a super clean bench at room temperature for 30 min, and then was placed on the RTCA Station in the incubator. After the system automatically scanned ("Scan Plate"), Step 2 was started to dynamically detect the cell proliferation curve in real time.

(5) E-Plate 16 was taken out, the target cell suspension and CNCT19 cell suspension were added to some of the wells, and the target cell suspension and untransfected T cell (i.e., NTD) suspension (as a control) were added to other wells, wherein the effector/target ratio (i.e., the ratio of the effector cells to the target cells, i.e., CNCT19 cells:target cells; and NTD:target cells) was 1:1, and the volume of the target cell suspension was 50 The E-Plate 16 detection plate was placed on the RTCA DP detection platform for 60 h real-time monitoring to observe the effect of CNCT19 cells on the target cells.

Figure 4:
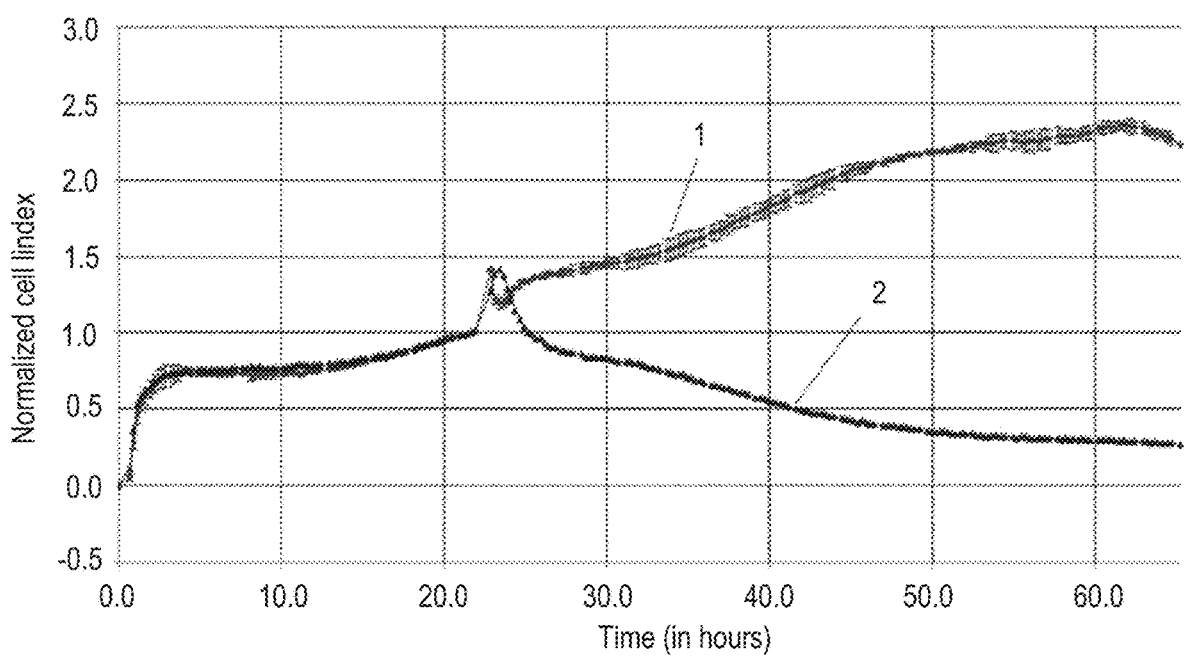
FIG. 4 shows killing of target cells (CHO-CD19) by CNCT19 cells as monitored in real time by the real-time cell analysis (RTCA) dual purpose (DP) system.

The results are shown in FIG. 4. In the figure, line 1 represents the curve of the NTD control group, and line 2 represents the curve of the CNCT19 treatment group. By comparing line 1 with line 2, it can be seen that the proliferation of tumor cells (i.e., target cells) was inhibited by CNCT19 cells with time. Specifically, after co-incubation with untransfected T cells, the target cells showed no significant change in the growth trend (line 1). In contrast, after co-incubation with CNCT19 cells, the target cells showed significantly decreased growth trend, and even started to show a decrease in their number (line 2). This shows that CNCT19 has strong killing ability against target cells.

Example 6

Detection of Secreted Cytokines After Co-Culture of CNCT19 Cells with Target Cells The experimental steps of this example are as follows:

1) The supernatant sample from the mixed culture in each well in Example 4 (i.e., the sample obtained in step 3) was taken out from the −20° C. refrigerator and melted at room temperature;

2) A LEGENDplex™ kit (manufacturer: Biolegend, catalog number: 740013) was used to treat each sample according to the instructions; and 3) The levels of different cytokines in each sample were detected by flow cytometry.

Figure 5A:
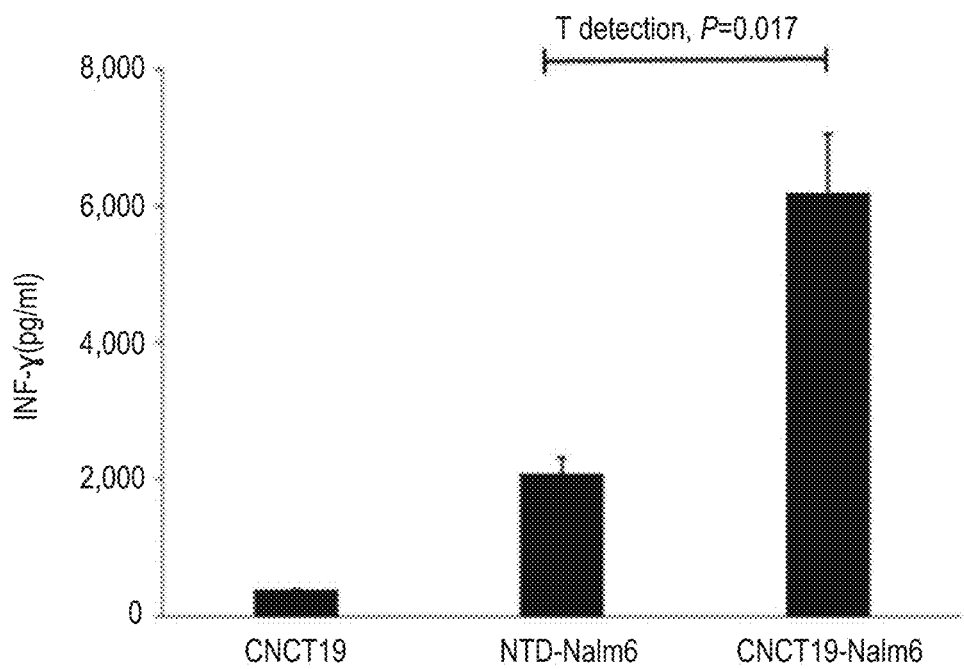
FIG. 5A shows variations of INF-γ concentrations in the supernatant under different co-culture conditions.
Figure 5B:
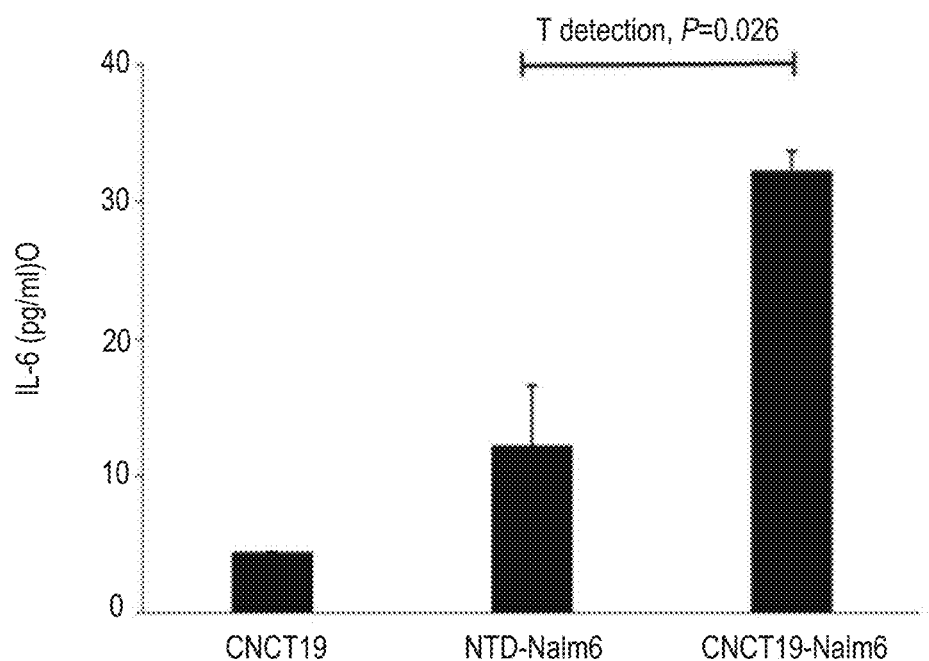
FIG. 5B shows variations of IL-6 concentrations in the supernatant under different co-culture conditions.

The results are shown in FIG. 5A and FIG. 5B. Compared with untransfected T cells (i.e., NTD), co-culture of CAR-T cells (i.e., CNCT19 cells) with Nalm-6 cells (CD19$^+$) resulted in a significantly increased secretion of the cytokines IFN-γ and IL-6 by CAR-T cells. Specifically, after co-cultured with the target cells at an effector/target ratio of 2:1 for 24 h, CNCT19 cells were stimulated by the target cells to secrete INF-γ in an amount of (6186.37±861.13) pg/ml, which was significantly higher than the amount of INF-γ (2096.85±228.16 pg/ml, $P<0.05$) secreted by the untransfected T cells; the amount of IL-6 (32.22±1.46 pg/ml) secreted by CNCT19 cells was significantly higher than that (12.23±4.37 pg/ml, $P<0.05$) secreted by the untransfected T cells.

Example 7

Detection of Hemolysis and Irritation of CNCT19 Cells 7.1. Test of Hemolysis of CNCT19 Cells In Vitro The experimental steps of this example are as follows:

1) A total of 7 glass test tubes were used and numbered 1 to 7, and to each tube was added 2.5 mL of 2% rabbit red blood cell suspension (harvested from New Zealand rabbits, and produced by the Chinese National Institutes for Food and Drug Control, with a number of quality certification of No. 11400500032425).

2) Different doses (0.5 to 0.1 mL) of CNCT19 cells at a concentration of $1\times10^7$ cells/mL (based on the total number of T cells) were added to tubes 1 to 5 which had already contained different doses (2.0 to 2.4 mL) of sodium chloride injection. Meanwhile, 2.5 mL of sodium chloride injection (negative control) and 2.5 mL of sterile water for injection (positive control) were added to tube 6 and tube 7, respectively.

3) Each test tube had a total volume of 5.0 mL. The test tubes were placed in a 37° C.±0.5° C. incubator for incubation for 3 h. Observation was made as to whether the red blood cells were lysed or aggregated at 15 min, 30 min, 45 min, 1 h, 2 h and 3 h after the test tubes were placed in the incubator.

Figure 6A:
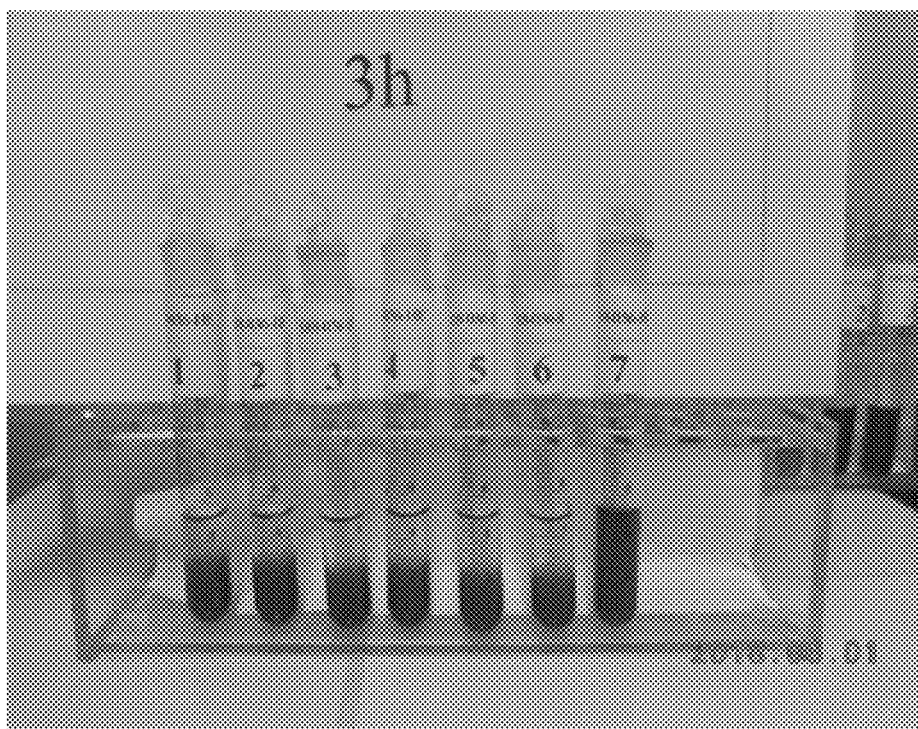
FIG. 6A shows observation results of each test tube before shaking for 3 hours.
Figure 6B:
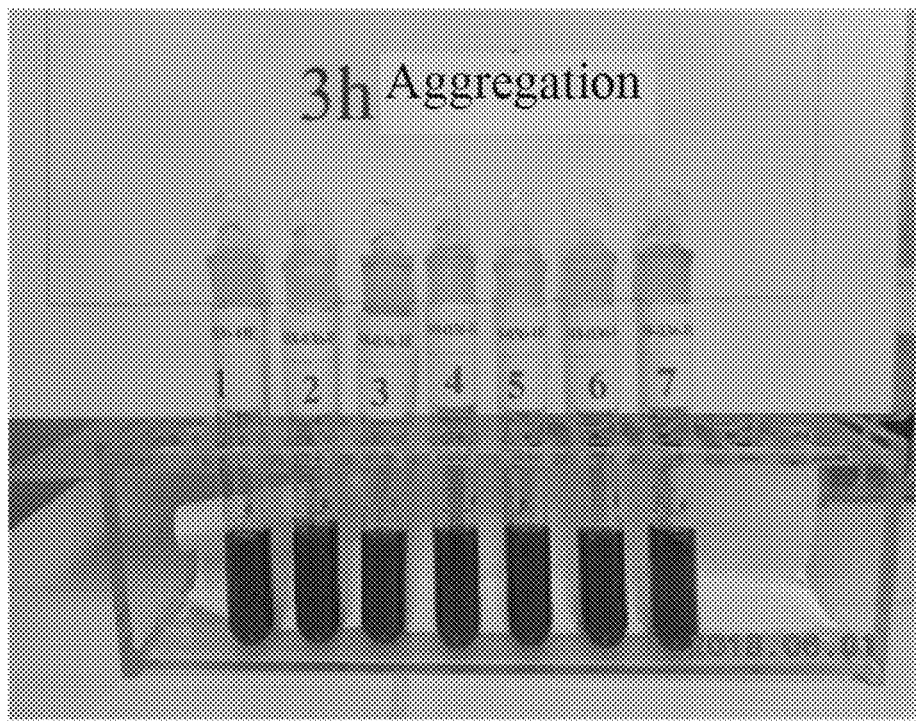
FIG. 6B shows observation results of each test tube after shaking for 3 hours.

The results are shown in FIG. 6A and FIG. 6B. FIG. 6A shows the observed results of each test tube before shaking for 3 h, and FIG. 6B shows the observed results of each test tube after shaking for 3 h. It can be seen that in the negative control tube (No. 6), the supernatant liquid was colorless and clear, and the red blood cells sank at the bottom of the tube, and they, after shaking, became evenly dispersed; it was judged that there was no hemolysis and no aggregation. In the positive control tube (No. 7), the solution was clear and red with no separated layers, and there was no red blood cell residue at the bottom of the tube; it was judged that there was complete hemolysis. By observing each of the test tubes to which different doses of CNCT19 cells were added for 3 h, it can be seen that the supernatant liquid in each test tube was colorless and clear, and the red blood cells sank at the bottom of the tube, and they, after shaking, became evenly dispersed; it was judged that there was no hemolysis and no aggregation.

7.2. Test of Vascular Irritation Upon Intravenous Infusion of CNCT19 Cells

The experimental steps of this example are as follows:

1) Six New Zealand rabbits (with three males and three females) that had passed the quarantine inspection and had no abnormalities in the injection sites were selected. A self-control method was used: cryopreserved CAR-T cells (i.e., CNCT19 cells) and a negative control (sodium chloride injection) were respectively intravenously infused into the right and left ears of each animal.

2) The CAR-T cells infused through the right ear-marginal veins were at a concentration of $1\times10^7$ cells/mL, and had a dosage of $1\times10^7$ cells/kg (based on the total number of T cells). The sodium chloride injection infected through the left ear-marginal veins was used as a negative control. The dosage intravenously administered through both the left and the right ear-marginal veins was 1 mL/kg.

3) After intravenous administration, general observation, observation of the injection sites, and pathological examination of the animals were carried out.

Figure 7A:
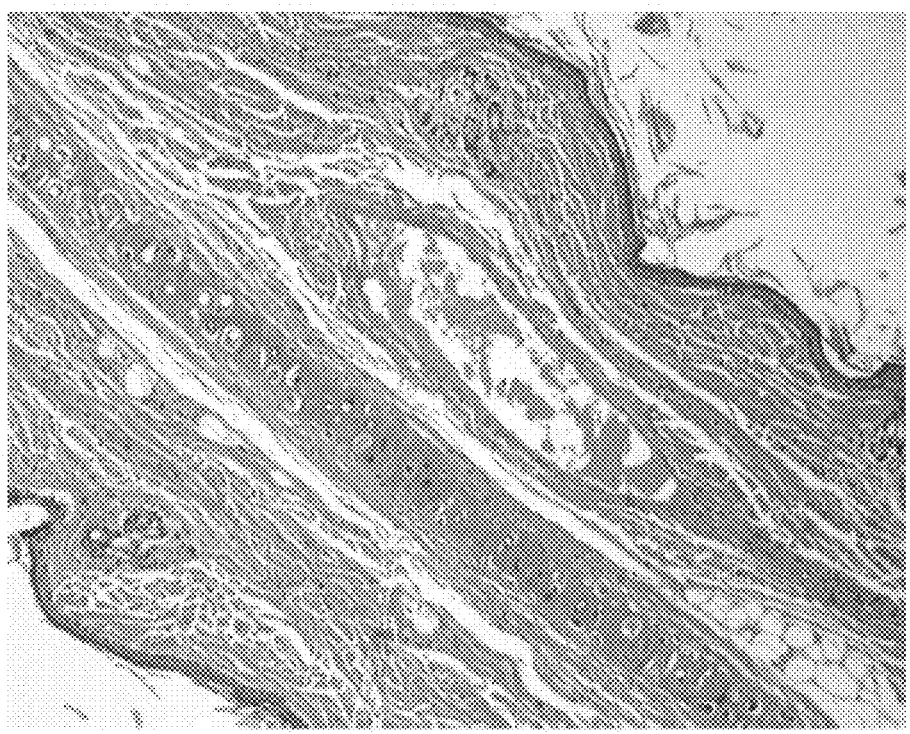
FIG. 7A shows a micrograph of the locally injected site after administration of the CAR-T cells (HE staining, 10× objective lens).
Figure 7B:
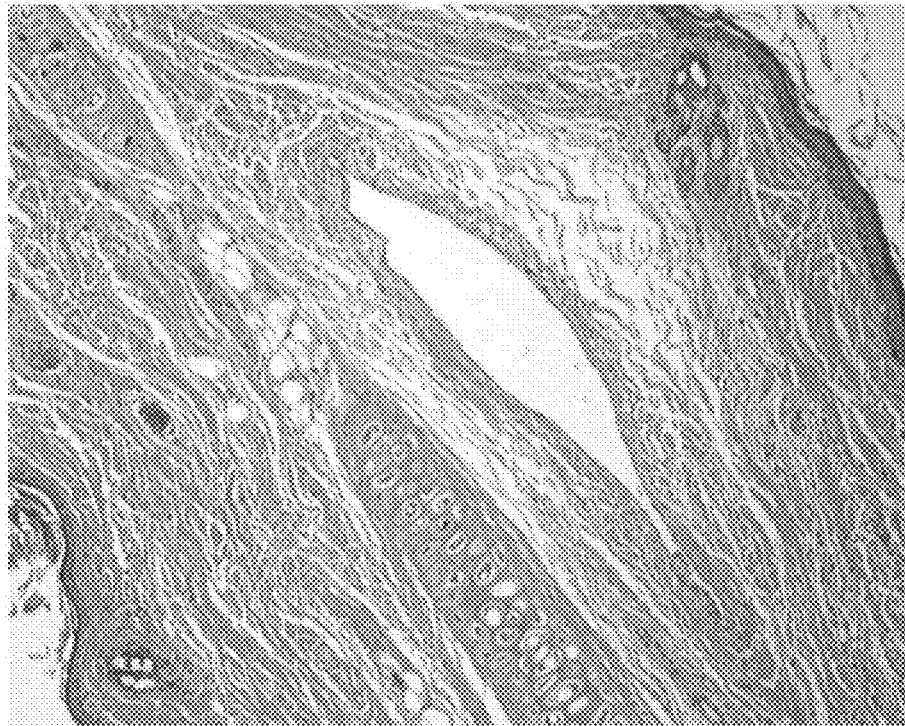
FIG. 7B shows a micrograph of the locally injected site after administration of sodium chloride injection solution (HE staining, 10× objective lens).

The results are shown in FIG. 7A and FIG. 7B. FIG. 7A shows a micrograph (HE-stained, 10× objective lens) of the injection site after the administration of CAR-T cells, and FIG. 7B shows a micrograph (HE-stained, 10× objective lens) of the injection site after the administration of sodium chloride injection. It can be seen that after intravenous infusion of the cryopreserved CAR-T cells, compared with the negative control side, no systemic or local symptoms and pathological abnormalities of the animals were found.

Example 8

Experiment of Oncogenicity of CNCT19 Cells In Vitro

The experimental steps of this example are as follows:

1) CAR-T cells (i.e., CNCT19 cells) from two donors were respectively incubated in soft agar medium. The two donors were Donor 1 (healthy human donor T Cells, lot number: TC20180613015) and Donor 2 (healthy human donor T Cells, lot number: TC20180613016), respectively. In addition, the human embryonic lung fibroblast cell line MRC-5 was set as a negative control, and the human cervical cancer cell line Hela was set as a positive control.

2) A 6-well culture plate was used in the experiment. The number of cells in each well was about $1\times10^3$, and three parallel wells were set for each group. The culture plate was placed in a $CO_2$ incubator for culture and observation was performed for 3 weeks.

3) The culture plate was taken out every 1 week to observe whether there was formation of clones with a microscope and take pictures. The experiment stopped until formation of obvious clone in the positive control group.

Figure 8:
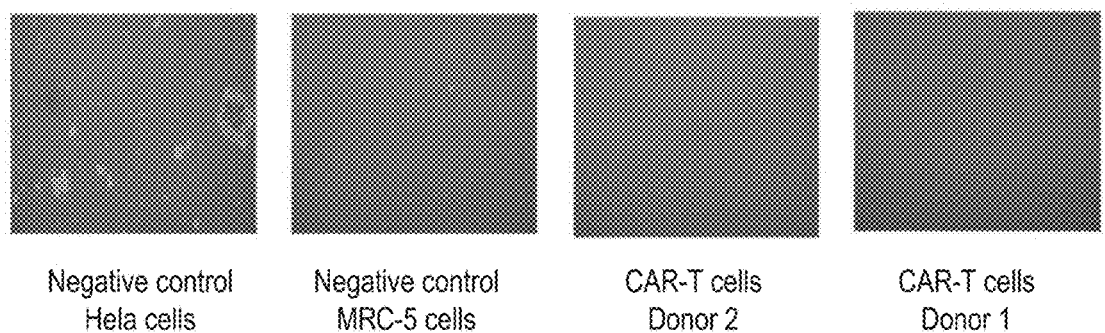
FIG. 8 shows soft-agar colony formation after 3 weeks of cell inoculation in each group.

The results are shown in FIG. 8. It can be seen that the positive control cells (Hela) formed clones in the culture medium, and the size of the clones increased significantly with time. On the 23rd day of observation, CAR-T cells from different donors and negative control cells (MRC-5) did not exhibit clonal growth, and they all died, not being characterized by immortalized proliferation in vitro.

Example 9

Experiment of Tumorigenicity of CNCT19 Cells In Vivo

The experimental steps of this example are as follows:

1) BALB/c nude mice were subcutaneously inoculated with cryopreserved CAR-T cells (i.e., CNCT19 cells) from two donors, and corresponding untransfected T cells (i.e., NTD), respectively, wherein the two donors were Donor 2 (healthy human donor T cells, lot number: TC20180613016) and Donor 3 (healthy human donor T cells, lot number: TC20180808019).

2) Inoculation with CAR-T cells was performed at $1\times10^7$ cells/mouse (based on the total number of T cells). The negative control group was inoculated with $1\times10^7$ human embryo lung fibroblast cell line MRC-5 cells per mouse, and the positive control group was inoculated with $1\times10^6$ human cervical cancer cell line Hela cells per mouse.

3) Continuous observation was performed for 16 weeks to detect whether there was a change in body weight, whether there were nodules generated, and whether the nodules would be induced to become tumorous nodules. The results were compared with those of the negative and positive cell groups.

4) After observation, gross anatomy was performed. Each organ was weighed, and the organ coefficient was calculated.

The inoculation sites and tissue or organs with suspicious symptoms were subjected to histopathologic examination.

The results show that CAR-T cells are not tumorigenic in vivo. In the negative control group (inoculated with MRC-5 cells), liquid nodules of all animals disappeared by the 9th day after inoculation. In the positive control group (inoculated with HeLa cells), the subcutaneous nodules of all animals slowly increased. Pathological examination showed that those nodules were caused by the growth of tumor tissue, with a tumor-forming rate of 100%. In summary, this experiment was valid. In the group inoculated with CAR-T cells (derived from two donors) and untransfected T cells, all the liquid nodules disappeared on the 5th day after inoculation, and no nodule formed again before euthanasia was performed on the 114th day. Pathological examination showed that there was no tumor formed at the sites of inoculation or metastasis.

Example 10

Test of Toxicity of Single Intravenous Injection of CNCT19 Cells to NCG Mice with Nalm-6 Xenograft Tumors The experimental steps of this example are as follows:

1) NCG mice aged 6-8 weeks were used, wherein half of them were male. Three days before the administration, Nalm-6 cell suspension was injected into the tail veins at a concentration of $2.5 \times 10^6$ cells/mL and at a dose of 10 mL/kg.

2) The screened animals were randomly divided into 4 sex-balanced groups according to their body weight (i.e., groups 2 to 5). Groups 2 to 5 were a vehicle control group, a T cell control group, and a CAR-T cell low-dose group and CAR-T cell high-dose group respectively, with 40 animals (20 males and 20 females) in each group. Both the non-tumor-bearing control group (i.e., group 1) and the vehicle control group (i.e., group 2) were given a vehicle control (i.e., physiological saline containing 4% (W/V) human albumin). The T cell control group (i.e., group 3) was given untransfected T cells (i.e., NTD) at a dose of $1 \times 10^9$ cells/kg (based on the total number of T cells, the same hereinafter). The CAR-T cell low-dose group (group 4) was inoculated at a dose of $1 \times 10^8$ cells/kg and the CAR-T cell high-dose group (group 5) was inoculated at a dose of $1 \times 10^9$ cells/kg.

3) The dosage for each animal was 25 mL/kg, the administration was performed by a single intravenous injection, and the rate of administration was about 1 mL/min.

4) After the administration, observation was continuously performed for 4 h on the day of administration. During the test, general clinical observation was carried out once in the morning and once in the afternoon each day. Detailed clinical observation and measurement of body weight and food intake were performed once a week. During the test, the body temperature, clinicopathological indicators (blood cell count and blood biochemical indexes) and immunological indicators (T lymphocyte subsets, cytokines and C-reactive protein) were detected.

5) In groups 1-5, 10 animals/sex/group were euthanized on day 2 and 5 animals/sex/group were euthanized on day 15. Their organs were weighed and gross anatomy observation was performed. The main organs of animals in groups 1 and 5 were subjected to histopathological examination.

The results of this experiment show that the maximum tolerated dose of CAR-T cells (i.e., CNCT19 cells) for a single administration was greater than $1 \times 10^9$ cells/kg. During the test, none of the animals in the CAR-T cell low-dose group and CAR-T cell high-dose group was dead or dying. No abnormal reaction was observed in either the general or the detailed clinical observation. No obvious abnormal changes in the body weight, food intake, body temperature, C-reactive protein, and blood biochemical indexes were observed. The histopathological examination found no obvious abnormality in the CAR-T cell low-dose group and CAR-T cell high-dose group as compared with the T cell control group.

Example 11

Treatment of Animals with CNCT19 Cells 11.1. Therapeutic Effect of CNCT19 Cells on NCG Mice with Nalm-6 Xenograft Tumors The experimental steps of this example are as follows:

1) Female NCG mice aged 6-8 weeks were used. Three days before the administration, $5 \times 10^5$ Nalm-6 cells were injected into the tail veins, wherein the Nalm-6 cells were dissolved in physiological saline at a concentration of $2.5 \times 10^6$ cells/ml, and each mouse was injected with 200 µl of cell resuspension.

2) Each experimental group was injected with corresponding CAR-T cells (i.e., CNCT19 cells), untransfected T cells (i.e., NTD) or cell preservation solution (i.e., physiological saline containing 4% (W/V) human albumin) A total of five groups were divided as follows: CAR-T low-dose group (injected with CNCT19 cells at $5 \times 10^6$ cells/mouse based on the total number of T cells, the same hereinafter), CAR-T medium-dose group (injected with CNCT19 cells at $1 \times 10^7$ cells/mouse), CAR-T high-dose group (injected with CNCT19 cells at $2 \times 10^7$ cells/mouse), T cell control group (injected with untransfected T cells at $2 \times 10^7$ cells/mouse) and vehicle control group (injected with cell preservation solution at 200 µl/mouse). The injection volume per mouse was 200 µl.

3) The body weight was detected and general clinical observation was performed twice a week. The survival of the mice was recorded and survival curves were plotted.

Figure 9:
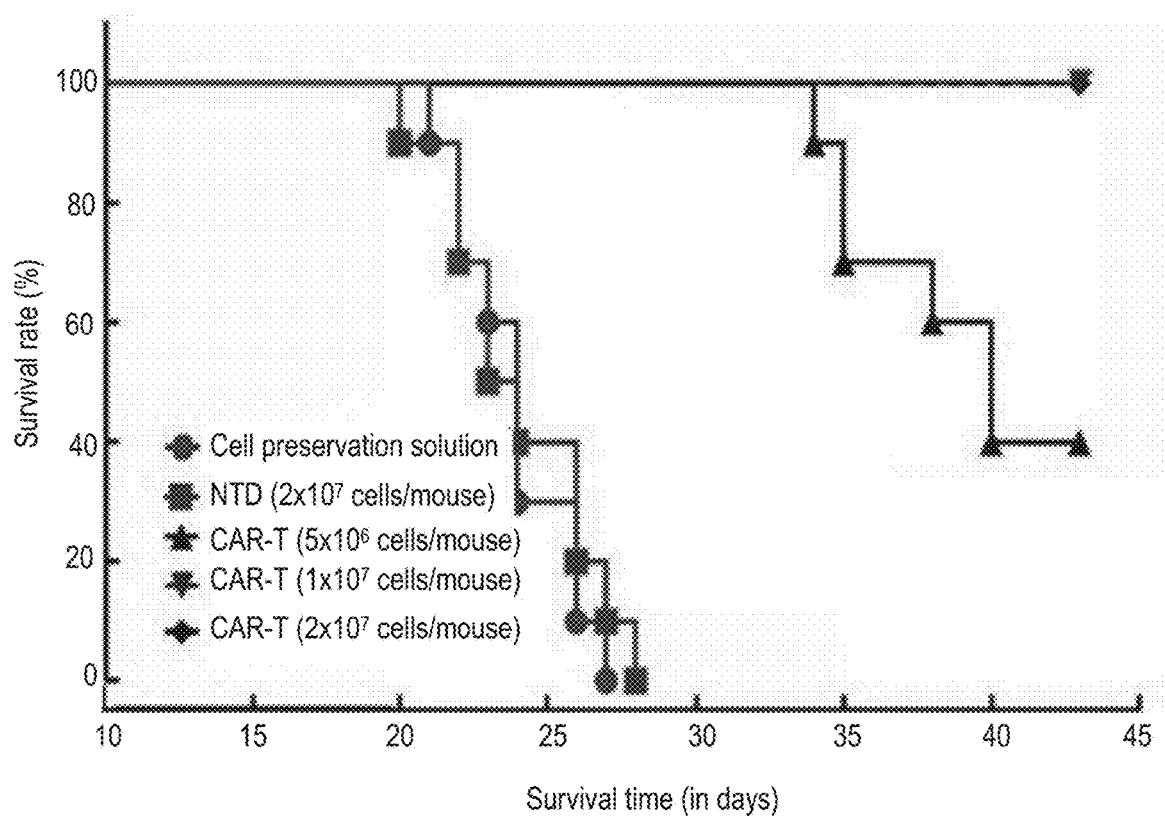
FIG. 9 shows survival curves of NCG mice with Nalm-6 xenograft tumors treated with different cells.

The results are shown in FIG. 9. As can be seen, CNCT19 cells at all doses have significant effects on prolonging the survival time and these effects are obviously dose-dependent. Specifically, the median survival time of the physiological saline control group was 24 days, that of the NTD control group was 23 days, and that of the CNCT19 low-dose group was 40 days, whereas all the experimental animals in the CNCT19 medium-dose group and the CNCT19 high-dose group survived to the end of the observation period. Compared with the physiological saline group and NTD control group, all the dose groups of CNCT19 can prolong the survival time of animals with leukemia by more than 16 days.

11.2. Distribution of CNCT19 Cells in Animals

The experimental steps of this example are as follows:

1) NCG mice aged 6-8 weeks were used, wherein half of them were male. Nalm-6 xenograft tumor models were established by the method in Example 11.1.

2) Both tumor-bearing and non-tumor-bearing animals received a single tail vein injection of CAR-T cells (i.e., CNCT19 cells) at a dose of $5 \times 10^6$ cells/mouse (based on the total number of T cells).

3) Animals in the tumor-bearing group were euthanized as planned at 24 hours (i.e., D2), 72 hours (i.e., D4), 168 hours (i.e., D8), 336 hours (i.e., D15), 504 hours (i.e., D22), and 672 hours (i.e., D29) respectively after the administration. The animals in the non-tumor-bearing group were euthanized as planned at 24 hours (i.e., D2), 168 hours (i.e., D8), and 336 hours (i.e., D15) respectively after the administration. Animal whole blood (EDTA anticoagulation), brain, spinal cord (cervical segment), skeletal muscle, gonads (ovaries, testes and epididymis), bladder, stomach, small intestine, mesenteric lymph nodes, bone marrow, liver, kidney, spleen, heart, lung and other tissues or body fluids were collected in order.

4) The content of chimeric antigen receptors (i.e., CARs) in blood and various tissue samples was determined using a validated Q-PCR method.

Figure 10:
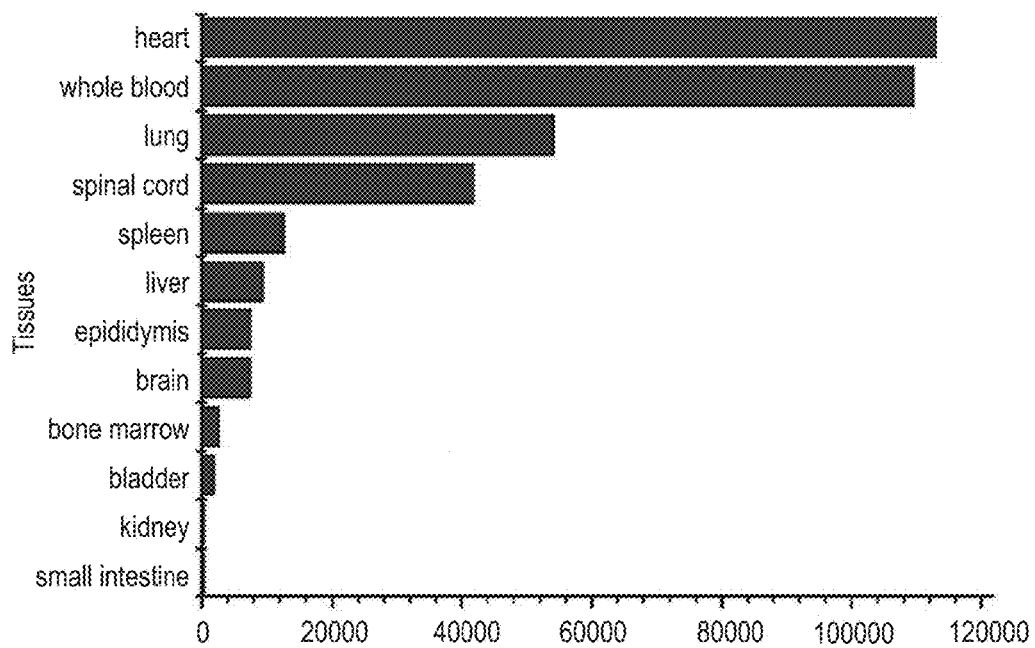
FIG. 10 shows distribution of tissues after single administration of CNCT19 cells.

The results show that after being administered to tumor-bearing mice and non-tumor-bearing mice by a single intravenous injection at a dose of $5 \times 10^6$ cells/mouse, the CNCT19 cells were mainly distributed in the whole blood and tissue with large blood flow such as lung, liver, heart, and spleen (see FIG. 10). Among them, heart and the whole blood had the largest distribution, with the areas under the areas under curve (the copy number of the nucleic acid molecule encoding CAR in gDNA-time, AUC) being about 150,000 hours*copy number/μg. The lung and spinal cord were followed, with AUC being about 40,000 to 60,000 hours*copy number/μg. As to spleen, liver and other tissue, AUC were less than about 20,000 hours*copy number/μg.

Figure 11:
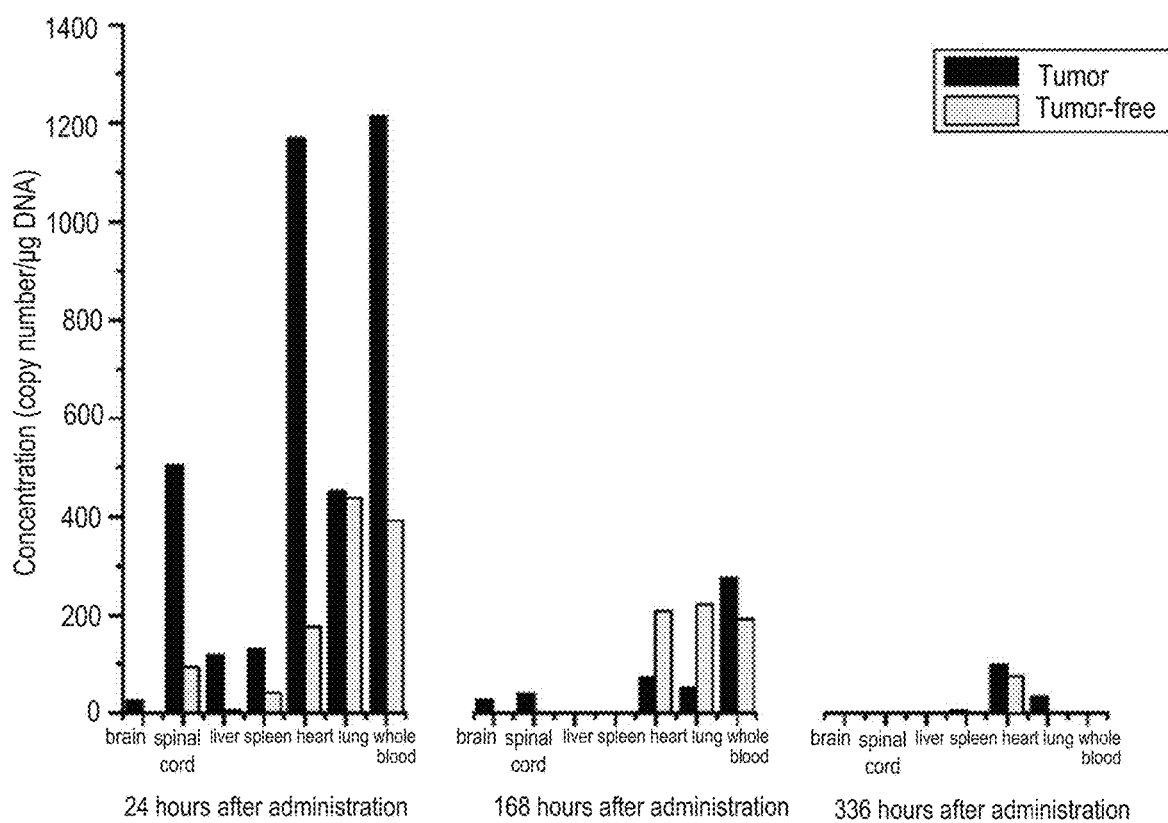
FIG. 11 is a comparison of the CNCT19 cells distributed in vivo in tumor-bearing and non-tumor-bearing animals

The results also show that the content of CNCT19 cells in the tissue of tumor-bearing mice was slightly higher than that of non-tumor-bearing mice (see FIG. 11). The concentrations of CNCT19 cells in the whole blood, heart and spinal cord of tumor-bearing mice were about 3 times, 6 times, and 5 times more than those in non-tumor-bearing mice 24 hours after administration.

Figure 12:
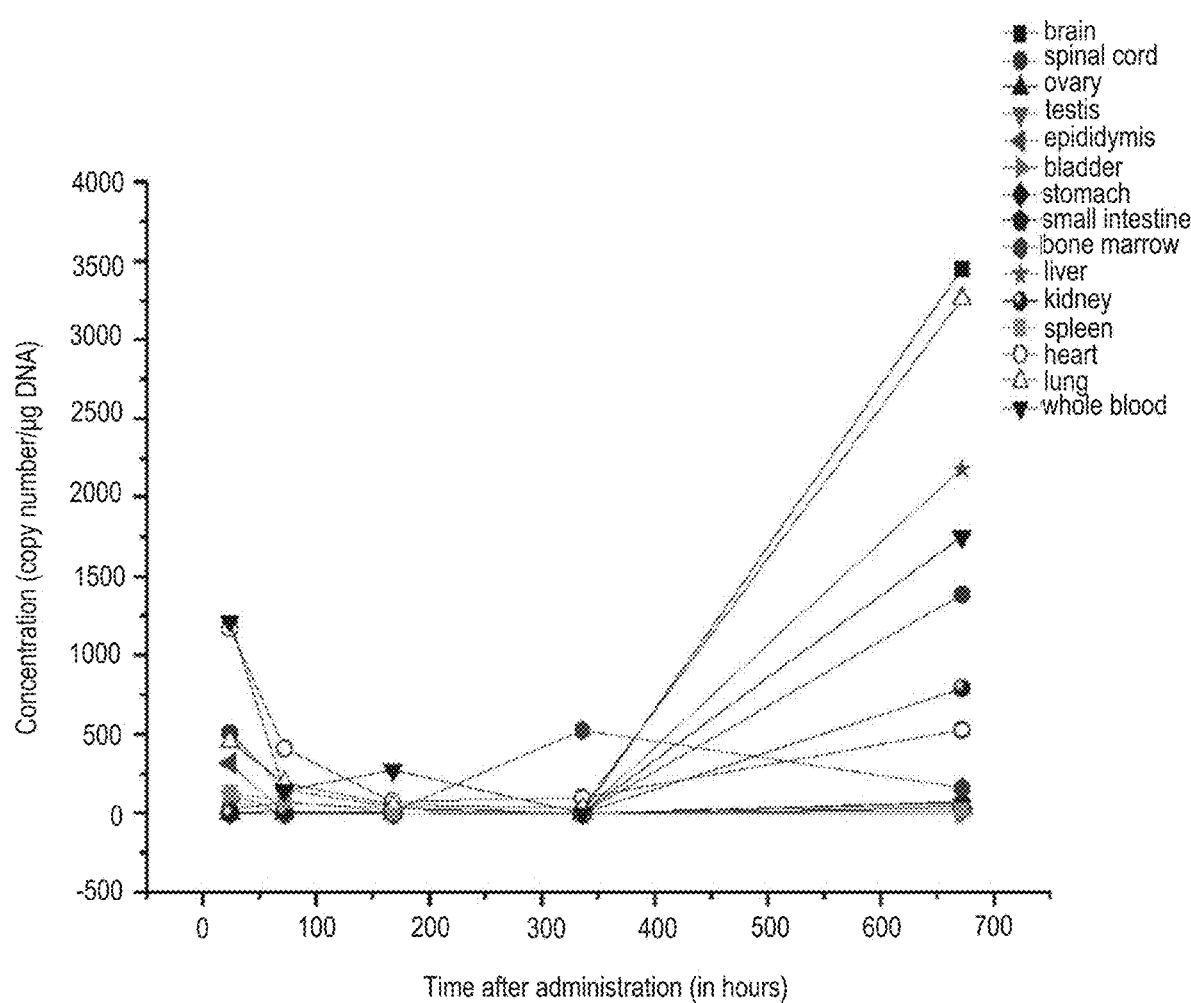
FIG. 12 shows variations in the CNCT19 cells distributed in various tissues of the animals after single administration.

Thereafter, the drug content in each tissue gradually decreased, and basically fell below the methodological detection limit two weeks after the administration. As the disease progressed, with enhancing CD19 antigen stimulation, the CNCT19 cells in the mice reactively proliferated again (see FIG. 12), wherein the concentration of CNCT19 cells in the brain, lung, liver, whole blood, and spinal cord increased to more than 1200 copies/μg DNA, and even reached 3500 copies/μg DNA.

Example 12

Treatment of Acute Lymphoblastic Leukemia with CNCT19 Cells 12.1. Clinical Use of CNCT19 Cells The clinical application process is shown in Table 3, and the specific experimental steps in some stages are described below.

TABLE 3

The process of clinical application of CNCT19 cells

| Visit | Date | Description |
| --- | --- | --- |
| Screening period | Week −6 to week −4 | Patients are screened ↓ |
| | Started in week −4 | PBMCs are collected by apheresis from the successfully screened subjects to prepare CNCT19 cell suspension, and the cell preparation takes 3-4 weeks ↓ |
| | Started on day −5 | The safety indexes are checked before the lymph node dissection pretreatment ↓ |
| | | The subjects are subjected to lymph node dissection pretreatment ↓ |
| | Started on day −1 | Baseline data are acquired ↓ |
| Treatment period | On day 0 | After the safety indexes are checked, the cells are reinfused ↓ |
| | On days 2, 4, 7, 10, 14 and 21 | A safety test is performed, and subjects are visited and examined and evaluated according to the research flow chart ↓ |
| | On day 28 | After completion of the treatment, an examination is performed, and the subjects are visited and examined and evaluated according to the research flow chart ↓ |
| Follow-up period | Performed once a month for 6 months | The subjects are visited and examined and evaluated according to the research flow chart ↓ |
| | Follow-up for the recurrence-free survival was performed once every three months | The subjects are visited and examined and evaluated according to the research flow chart |
| | Follow-up for the overall survival was performed once every three months for 2 years | Follow-up can be completed by telephone to obtain information on the survival status of the subjects and their anti-tumor treatment |

1. Lymph Node Dissection Pretreatment

Lymph node dissection pretreatment is performed on day −5 before the CNCT19 cell suspension is reinfused as planned.

The pretreatment schemes are as follows:

Fludarabine is administered at 30 mg/m$^2$ once per day for 2-4 consecutive days; and cyclophosphamide is administered at 500 mg/m$^2$ once per day for 2 consecutive days.

The use of the two drugs for the pretreatment chemotherapy should be started from the same day.

2. Reinfusion of CNCT19 Cell Suspension (1) After the cells are successfully prepared, they are cryopreserved under the condition of <−100° C., transported to the hospital under the same temperature condition for use, and recovered according to the experiment operation guide before infusion.

(2) The method for reinfusing cells is as follows. The cells are recovered according to the experiment operation guide, and the reinfusion of the cell suspension should be complete within 30 minutes after the recovery. The cell suspension is infused as a single infusion into the subject through a vein with a blood transfusion device. If there is more than one bag of cell suspension, they can be continuously infused without time interval between reinfusion of each bag. The subject needs to be closely observed during the cell reinfusion. If a serious adverse event occurs, the infusion should be stopped, and corresponding treatment should be performed according to the specific adverse event. If no serious adverse event occurs, follow-up can be carried out in accordance with the visit workflow.

(3) The subject needs to be closely observed for 24 h after the cell reinfusion. If a serious adverse event occurs, corresponding treatment should be performed according to the specific adverse event. If no serious adverse event occurs, follow-up can be carried out in accordance with the visit workflow.

(4) After the cell reinfusion, the subject needs to continue to be hospitalised for observation for 14 days or for a duration determined according to the researcher's comprehensive assessment of the subject's condition.

3. Management of CNCT19 Cell Suspension

In order to strictly manage and use the CNCT19 cell suspension, a strict system of managing CNCT19 cell suspension by specifically assigned personnel has been established. Specific personnel are assigned to transport the cell suspension for research to the hospital departments, and specific personnel are assigned responsibility for the reception of the cell suspension for research and the establishment of a registration system.

After the infusion, the packaging of the cell suspension is recovered and stored/destroyed by the drug management personnel.

4. The clinical efficacy and safety results of CNCT19 cell suspension in the treatment of relapsed or refractory acute lymphoblastic leukemia This experiment started from September 2016 to October 2020. During the exploratory and phase I clinical trials, 63 patients with relapsed or refractory acute lymphoblastic leukemia (ALL) (with 23 adult patients and 40 children patients) were treated with CNCT. The explored dose administered for adult ALL ranged from 0.25×10$^8$ to 0.5×10$^8$ CAR-positive T cells.

(a) The data on the clinical efficacy are shown in Table 4 and Table 5. Table 4 shows the recovery of 63 patients including adults and children. Table 5 shows the recovery of the 23 adult patients. It can be seen that among the 63 patients with relapsed or refractory acute lymphoblastic leukemia, after the injection and reinfusion of the CNCT19 cell suspension, the vast majority (93.7%) of the patients were in complete remission, and 88.9% of the patients were MRD negative. The results show that injection and reinfusion of the CNCT19 cell suspension can effectively treat adult patients and children patients with relapsed or refractory acute lymphoblastic leukemia.

TABLE 4

The clinical efficacy of the CNCT19 cell suspension on treating acute lymphoblastic leukemia in adults and children Adults and children with relapsed or refractory acute lymphoblastic leukemia

N = 63

| | |
|---|---|
| ORR | 93.7% (59/63) |
| CR/Cri | 93.7% (59/63) |
| MRD negative | 88.9% (56/63) |

TABLE 5

The clinical efficacy of the CNCT19 cell suspension on treating acute lymphoblastic leukemia in adults Adults with relapsed or refractory acute lymphoblastic leukemia

N = 23

| | |
|---|---|
| ORR | 91.3% (21/23) |
| CR/Cri | 91.3% (21/23) |
| MRD negative | 86.9% (20/23) |

Note:

in Tables 4 and 5,

ORR stands for overall remission rate;

MRD (Minimal Residual Disease) negative means no tumor cell is detected (by the most sensitive method);

CR stands for complete remission; and

Cri stands for morphologic complete remission with incomplete blood count recovery.

b) The data of the preliminary safety results are shown in Table 6 and Table 7. Table 6 shows the safety results for 63 patients including adult and children patients, and Table 7 shows the safety results for 23 adult patients. Among the 63 ALL patients, the incidence of grade 3 and above CRS and that of encephalopathy were 19% and 20.6%, respectively. A comparison between the age groups reveals that the incidence (39.1%) of severe CRS in the adult group is higher than that (7.5%) in the child group, and the incidence (17.4%) of severe CRES in the adult group is slightly lower than or close to that (22.6%) in the child group. This may be due to the fact that in the early trials CNCT19 was given according to body weight, and the adult patients with larger body weight received higher doses. For example, the dose given to the 46 subjects in the early trials ranged from 0.71×10$^6$ to 4.08×10$^6$/kg, equivalent to 0.16×10$^8$-2.36×10$^8$ CAR-positive T cells. As the initial dose-exploration gradually shed light on the characteristics of CNCT19 products, a safer dose range was selected in subsequent clinical studies. For example, among the 17 patients receiving a dose ranging from 0.2×10$^8$ to 1.1×10$^8$ CAR-positive T cells (median value: 0.5×10$^8$), the incidence of grade ≥3 CRS and CRES dropped to 5.9% (1/17).

It can be seen that injection of the CNCT19 cell suspension has a low probability of causing severe CRS or CRES side effects, its overall safety is controllable, and thus CNCT19 has good safety performance. The good safety performance of CNCT19 improves the quality of the products and reduces the clinical risks.

TABLE 6

The safety results of the CNCT19 cell suspension for adults and children with acute lymphoblastic leukemia

|  |  | Cytokine Release Syndrome (CRS) | | CAR-T-cell-related Encephalopathy Syndrome (CRES) | |
|---|---|---|---|---|---|
|  |  | All grades | Grade ≥3 | All grades | Grade ≥3 |
| Adults + children with acute lymphoblastic leukemia | Total (n = 63) | 54 (85.7%) | 12 (19%) | 22 (34.9%) | 13 (20.6%) |

TABLE 7

The safety results of the CNCT19 cell suspension for adults with acute lymphoblastic leukemia

|  |  | Cytokine Release Syndrome (CRS) | | CAR-T-cell-related Encephalopathy Syndrome (CRES) | |
|---|---|---|---|---|---|
|  |  | All grades | Grade ≥3 | All grades | Grade ≥3 |
| Adults with acute lymphoblastic leukemia | Total (n = 23) | 20 (869%) | 9 (39.1%) | 8 (34.8%) | 4 (174%) |

Note:
in Tables 6 and 7,
CRS stands for cytokine release syndrome; and
CRES stands for CAR-T-cell-related encephalopathy syndrome.

Example 13

Treatment of Relapsed or Refractory Non-Hodgkin's Lymphoma with CNCT19 Cells 13.1. Clinical Use of CNCT19 Cells The clinical application process is shown in Table 8, and the specific experimental steps in some stages are described below.

TABLE 8

The process of clinical application of CNCT19 cells

| Visit | Date | Description |
|---|---|---|
| Screening period | Week −8 to the time before the apheresis | Patients are screened ↓ |
|  | Week −7 to day −1 | PBMCs are collected by apheresis from the successfully screened subjects to prepare CNCT19 cell suspension, and the cell preparation takes 3-4 weeks ↓ |
|  | Day −5 to day −2 | The safety indexes are checked before the lymph node dissection pretreatment ↓ |
|  |  | The subjects are subjected to lymph node dissection pretreatment ↓ |
|  | Started on day −1 | Baseline data are acquired ↓ |
|  | On day 0 | After the safety indexes are checked, the cells are reinfused ↓ |
| Treatment period | On days 2, 4, 7, 10, 14 and 21 | A safety test is performed, and subjects are visited and examined and evaluated according to the research flow chart ↓ |
|  | On day 28 | After completion of the treatment, an examination is performed, and the subjects are visited and examined and evaluated according to the research flow chart ↓ |
| Follow-up period | Follow-up for the overall remission rate was performed once a month for 6 months | The subjects are visited and examined and evaluated according to the research flow chart ↓ |
|  | Follow-up for the recurrence-free survival was performed once every three months | The subjects are visited and examined and evaluated according to the research flow chart |
|  | Follow-up for the overall survival was performed once every three months for 2 years | Follow-up can be completed by telephone to obtain information on the survival status of the subjects and their anti-tumor treatment |

1. Lymph Node Dissection Pretreatment

Lymph node dissection pretreatment is performed on day −5 before the CNCT19 cell suspension is reinfused as planned.

The pretreatment schemes are as follows:

Fludarabine is administered at 30 mg/m$^2$ once per day for 2-4 consecutive days; and cyclophosphamide is administered at 500 mg/m$^2$ once per day for 2 consecutive days.

The use of the two drugs for the pretreatment chemotherapy should be started from the same day.

2. Reinfusion of CNCT19 cell suspension (1) After the cells are successfully prepared, they are cryopreserved under the condition of <−100° C., transported to the hospital under the same temperature condition for use, and recovered according to the experiment operation guide before infusion.

(2) The method for reinfusing cells is as follows. The cells are recovered according to the experiment operation guide, and the reinfusion of the cell suspension should be complete within 30 minutes after the recovery. The cell suspension is infused as a single infusion into the subject through a vein with a blood transfusion device. If there is more than one bag of cell suspension, they can be continuously infused without time interval between reinfusion of each bag. The subject needs to be closely observed during the cell reinfusion. If a serious adverse event occurs, the infusion should be stopped, and corresponding treatment should be performed according to the specific adverse event. If no serious adverse event occurs, follow-up can be carried out in accordance with the visit workflow.

(3) The subject needs to be closely observed for 24 h after the cell reinfusion. If a serious adverse event occurs, corresponding treatment should be performed according to the specific adverse event. If no serious adverse event occurs, follow-up can be carried out in accordance with the visit workflow.

(4) After the cell reinfusion, the subject needs to continue to be hospitalised for observation for 14 days or for a duration determined according to the researcher's comprehensive assessment of the subject's condition.

3. Management of CNCT19 Cell Suspension

In order to strictly manage and use the CNCT19 cell suspension, a strict system of managing CNCT19 cell suspension by specifically assigned personnel has been established. Specific personnel are assigned to transport the cell suspension for research to the hospital departments, and specific personnel are assigned responsibility for the reception of the cell suspension for research and the establishment of a registration system.

After the infusion, the packaging of the cell suspension is recovered and stored/destroyed by the drug management personnel.

4. The Clinical Efficacy and Safety Results of CNCT19 Cell Suspension in the Treatment of Relapsed or Refractory Non-Hodgkin's Lymphoma This experiment started from September 2016 to October 2020. During the exploratory and phase I clinical trials, 50 patients with relapsed or refractory non-Hodgkin's lymphoma (NHL) were treated with CNCT19 cell suspension. The explored dose administered for NHL (in adults only) ranged from 1×10$^8$ to 2×10$^8$ CAR-positive T cells.

(a) The data on the clinical efficacy are shown in Table 9. Table 9 shows the recovery of 50 patients. It can be seen that among the 50 patients with relapsed or refractory non-Hodgkin's lymphoma, after the injection and reinfusion of the CNCT19 cell suspension, about 80% of the patients were in complete remission or partial remission, wherein the rate of complete remission was 54% (27 cases) and the rate of partial remission was 24% (12 cases). This shows that the CNCT19 cell suspension can effectively treat patients with relapsed or refractory non-Hodgkin's lymphoma.

TABLE 9

The clinical efficacy of the CNCT19 cell suspension on treating non-Hodgkin's lymphoma
Relapsed or refractory non-Hodgkin's lymphoma
N = 50

| | |
|---|---|
| ORR | 78% (39/50) |
| CR | 54% (27/50) |
| PR | 24% (12/50) |

Note:
in TABLE 9,
ORR stands for overall remission rate;
CR stands for complete remission; and
PR stands for partial remission.

b) The data of the preliminary safety results are shown in Table 10. Table 10 shows the safety results for 50 patients. It can be seen that injection of the CNCT19 cell suspension has a low probability of causing severe CRS or CRES side effects, and has a probability of causing Grade≥3 side effects of lower than 10%, wherein the probability of causing Grade≥3 CRS is 0% and the probability of causing Grade≥3 CRES is 6%. Thus, CNCT19 has good safety performance.

TABLE 10

The safety results of the CNCT19 cell suspension for non-Hodgkin's lymphoma

| | | Cytokine Release Syndrome (CRS) | | CAR-T-cell-related Encephalopathy Syndrome (CRES) | |
|---|---|---|---|---|---|
| | | All grades | Grade ≥3 | All grades | Grade ≥3 |
| Non-Hodgkin's lymphoma | Total (n = 50) | 30 (60%) | 0 (0) | 3 (6%) | 3 (6%) |

Note:
in TABLE 10,
CRS stands for cytokine release syndrome; and
CRES stands for CAR-T-cell-related encephalopathy syndrome.

The foregoing detailed description is provided by way of explanation and example, but is not intended to limit the scope of the attached claimed. The various changes to the embodiments enumerated in the disclosure are apparent to one of ordinary skill in the art and are retained within the scope of the attached claims and equivalents thereof.

The invention claimed is:

1. A plasmid combination, wherein the plasmid combination comprises plasmids Seq1, PMD2.G, pMDLg-pRRE and pRSV-Rev; and the plasmids Seq1, PMD2.G, pMDLg-pRRE and pRSV-Rev are present at a ratio of 2-6: 1-1.5: 1-31-1.5;
wherein the plasmid Seq1 comprises a nucleic acid molecule encoding a chimeric antigen receptor, and wherein the chimeric antigen receptor comprises an amino acid sequence shown in SEQ ID NO. 1.

2. The plasmid combination according to claim 1, wherein the plasmid Seq1 comprises a nucleic acid molecule encoding a chimeric antigen receptor, wherein the nucleic acid molecule comprises a nucleic acid sequence shown in SEQ ID NO. 2.

3. A plasmid combination, wherein the plasmid combination comprises plasmids Seq1, PMD2.G, pMDLg-pRRE and pRSV-Rev; and the plasmids Seq1, PMD2.G, pMDLg-pRRE and pRSV-Rev are present at a ratio of 11.8: 3.53: 6.33: 2.3, 13.8: 3.48: 5.31: 2.54 or 14: 4.67: 4.67: 4.67;
wherein the plasmid Seq1 comprises a nucleic acid molecule encoding a chimeric antigen receptor, and wherein the chimeric antigen receptor comprises an amino acid sequence shown in SEQ ID NO. 1.

4. A method for preparing a lentiviral vector, the method comprising introducing the plasmid combination according to claim 1 into a cell.

5. The method according to claim 4, wherein the cell is 293T.

6. A method for preparing a modified immune effector cell, comprising preparing the lentiviral vector according to the method according to claim 4.

7. The method according to claim 6, comprising introducing the lentiviral vector into an immune effector cell.

8. The method according to claim 7, wherein the immune effector cell is selected from the group consisting of a T lymphocyte and a natural killer cell.

9. A modified immune effector cell prepared by the method according to claim 6.

10. The modified immune effector cell according to claim 9, wherein the chimeric antigen receptor is expressed on the surface of the immune effector cell.

11. A composition comprising the modified immune effector cell according to claim 9.

12. The plasmid combination according to claim 1, wherein the plasmids Seq1, PMD2.G, pMDLg-pRRE and pRSV-Rev are present at a ratio of 3-6: 1-1.5: 1-3: 1-1.5.

13. The plasmid combination according to claim 1, wherein the plasmid Seq1 does not comprise GFP gene.

14. The plasmid combination according to claim 1, wherein the plasmid Seq1 does not comprise T2A gene.

15. The plasmid combination according to claim 1, wherein the plasmid Seq1 does not comprise ampicillin resistance gene.

16. The plasmid combination according to claim 1, wherein the plasmid Seq1 comprises kanamycin resistance gene.

17. The method according to claim 4, wherein the cell is 293T/17.

* * * * *

UNITED STATES PATENT AND TRADEMARK OFFICE
CERTIFICATE OF CORRECTION

PATENT NO. : 11,497,771 B2
APPLICATION NO. : 17/412617
DATED : November 15, 2022
INVENTOR(S) : Yun Liu et al.

It is certified that error appears in the above-identified patent and that said Letters Patent is hereby corrected as shown below:

On the Title Page

Column 1, below item (63) ("Related U.S. Application Data"), insert the following:
--(30) Foreign Application Priority Data
Dec. 17, 2019 (CN) ............... 201911301518.8
Nov. 16, 2020 (CN) ............... 202011274810.8
Dec. 10, 2020 (CN) ............... 202011433671.9--.

In the Claims

In Claim 1, Column 37, Line 16, "1-31-1.5" should read --1-3:1-1.5--.

Signed and Sealed this
Twenty-first Day of March, 2023

Katherine Kelly Vidal
*Director of the United States Patent and Trademark Office*